(12) United States Patent  
Sprigg et al.

(10) Patent No.: US 9,041,530 B2  
(45) Date of Patent: May 26, 2015

(54) BIOMETRIC ATTRIBUTE ANOMALY DETECTION SYSTEM WITH ADJUSTING NOTIFICATIONS

(75) Inventors: Stephen A. Sprigg, Poway, CA (US); Richard Wayne Gardner, III, Rancho Santa Fe, CA (US)

(73) Assignee: QUALCOMM Incorporated, San Diego, CA (US)

( * ) Notice: Subject to any disclaimer, the term of this patent is extended or adjusted under 35 U.S.C. 154(b) by 322 days.

(21) Appl. No.: 13/464,087

(22) Filed: May 4, 2012

(65) Prior Publication Data

US 2013/0278414 A1 Oct. 24, 2013

Related U.S. Application Data

(60) Provisional application No. 61/625,778, filed on Apr. 18, 2012.

(51) Int. Cl.
| | |
|---|---|
| *G08B 1/08* | (2006.01) |
| *G08B 21/02* | (2006.01) |
| *G08B 21/04* | (2006.01) |

(52) U.S. Cl.  
CPC ............ *G08B 21/02* (2013.01); *G08B 21/0453* (2013.01)

(58) Field of Classification Search  
CPC .......... A61B 5/411; A61B 5/002; A61B 5/00; G08B 21/02; G06F 19/3418  
USPC ................. 340/539.1, 539.12, 539.13, 573.1; 600/300  
See application file for complete search history.

(56) References Cited

U.S. PATENT DOCUMENTS

| | | | | |
|---|---|---|---|---|
| 6,160,478 | A  * | 12/2000 | Jacobsen et al. | 340/539.12 |
| 7,292,139 | B2 * | 11/2007 | Mazar et al. | 340/531 |
| 7,301,451 | B2 * | 11/2007 | Hastings | 340/539.12 |
| 7,382,247 | B2 | 6/2008 | Welch et al. | |

(Continued)

FOREIGN PATENT DOCUMENTS

CN 101732041 A 6/2010

OTHER PUBLICATIONS

Basak, A, et al. "KiMS: Kids' Health Monitoring System at day-care centers using wearable sensors and vocabulary-based acoustic signal processing"; 13th IEEE International Conference; Jun. 13-15, 2011; e-Health Networking Applications and Services (Healthcom); pp. 1-8.

(Continued)

*Primary Examiner* — Eric M Blount  
(74) *Attorney, Agent, or Firm* — Gerald P. Joyce, III

(57) ABSTRACT

A system, methods and server for monitoring health and safety of individuals in a population and sending alert notifications when exceptions are detected include comparing biometric data obtained from the individuals to a biometric model generated for the individual through computer-learning methods. Biometric data may be gathered by wireless biometric sensor devices which transmit biometric data to receiver devices, which relay the biometric data to a server. The biometric model may be maintained in the server and include nominal and threshold biometric parameters for each individual based on biometric sensor data gathered or analyzed over a period of time. An alert may be issued by the server when an individual's biometric data is outside a threshold in the biometric model. The transmitted alert may depend upon the nature of the exception, user settings and past notification experience. Alerts may be escalated when not answered within defined durations.

90 Claims, 8 Drawing Sheets

(56) References Cited

U.S. PATENT DOCUMENTS

| | | | |
|---|---|---|---|
| 7,598,878 B2 | 10/2009 | Goldreich | |
| 7,616,110 B2 | 11/2009 | Crump et al. | |
| 7,636,047 B1* | 12/2009 | Sempek | 340/572.8 |
| 8,157,730 B2* | 4/2012 | LeBoeuf et al. | 600/301 |
| 8,591,411 B2* | 11/2013 | Banet et al. | 600/300 |
| 2003/0149593 A1 | 8/2003 | Mok et al. | |
| 2004/0078219 A1* | 4/2004 | Kaylor et al. | 705/2 |
| 2004/0100376 A1* | 5/2004 | Lye et al. | 340/539.12 |
| 2004/0172290 A1* | 9/2004 | Leven | 705/2 |
| 2005/0228300 A1 | 10/2005 | Jaime et al. | |
| 2010/0023348 A1 | 1/2010 | Hardee et al. | |
| 2010/0217098 A1 | 8/2010 | Leboeuf et al. | |
| 2011/0201901 A1 | 8/2011 | Khanuja | |
| 2012/0316932 A1* | 12/2012 | Rahman et al. | 705/14.1 |
| 2013/0271279 A1* | 10/2013 | Mazar et al. | 340/539.12 |
| 2014/0104059 A1* | 4/2014 | Tran | 340/539.12 |

OTHER PUBLICATIONS

International Search Report and Written Opinion—PCT/US2013/037059—ISA/EPO—Mar. 21, 2014.

* cited by examiner

BIOMETRIC ATTRIBUTE ANOMALY DETECTION SYSTEM WITH ADJUSTING NOTIFICATIONS

RELATED APPLICATIONS

This application claims the benefit of priority to U.S. Patent Application No. 61/625,778 entitled "Biometric Attribute Anomoly Detection System With Adjusting Notifications" filed Apr. 18, 2012, the entire contents of which are hereby incorporated by reference.

BACKGROUND

Schools, adult care facilities, penal institutions, and other entities that deal in significant population management encounter enormous difficulty observing health and physical characteristics of individuals under their supervision. Illness and injury are persistent threats to the general health and safety of groups of individuals when they spend substantial time in close proximity. Detecting illnesses or injury early can be difficult in the initial phases, particularly for children who may not recognize their own symptoms. The longer a sick individual remains in the population, the greater the risk of infecting others.

SUMMARY

The various embodiments provide a system for wireless monitoring of individuals within a defined space that can detect an exception condition and respond with configurable, graduated measures. The system may employ wireless biometric sensor devices to relay real-time data about individuals' physical states to a server. Current biometric measurements may be evaluated for anomalies using biometric models, which may be derived from previous sensor measurements, external variables, and configured parameters. If the server discerns the existence of an anomalous condition, the system may transmit dynamic alert notifications to caregivers that correspond to the urgency and nature of the situation. Thus, health and safety concerns may be automatically detected and addressed without human interaction or a significant number of false alarms.

The various embodiments include methods, which may be implemented a server as part of a system, monitoring a population of individuals for health and safety, including generating a biometric model of nominal and threshold biometric parameters for each individual of the population based on biometric sensor data obtained by one or more biometric sensors and transmitted wirelessly from a plurality of wireless biometric sensor devices which are connected to the sensors and carried by the individuals of the population.

The biometric model for each individual may be generated by the server analyzing received biometric sensor data for each individual over a period of time to calculate average and threshold values for each biometric parameter as a function of scheduled activities. This biometric model may be used to monitor individuals in a system in which the plurality of wireless biometric sensor devices transmit current biometric sensor data to a server. The biometric parameters measured by the biometric sensors may include one or more of temperature, acceleration, pulse rate, blood pressure, blood oxygen level, blood sugar level, pH of skin, and presence of perspiration. The system or server may process the biometric data by associating the current biometric sensor data received from each of the plurality of mobile devices with a respective individual, evaluating the current biometric sensor data for the individual using the biometric model for that individual, determining whether an exception condition exists by noting when the current biometric sensor data is outside of a nominal range of at least one biometric parameter for the individual. The server may also update the biometric model for the individual based on the current biometric sensor data. The biometric model for each individual may be determined by the server analyzing received biometric sensor data for each individual over a period of time to calculate average and threshold values for each biometric parameter as a function of temporal conditions. The server may maintain the biometric model evaluate the current biometric sensor data for the individual using the biometric model for that individual by comparing the current biometric sensor data for the individual to nominal ranges of the biometric parameters for that individual in similar temporal conditions, scheduled activities, temperatures, particular locations, and atmospheric conditions. The biometric model may be continuously updated, such as by identifying dependencies between various biometric parameters over time, adjusting nominal and threshold values to represent the current biometric sensor data, learning from operator feedback (e.g., feedback that an individual really was or was not sick or injured at particular time).

The server may transmit an alert notification in response to determining the exception condition. The type of alert notification generated and the recipients of the alert may be determined based on the exception condition. Alert notifications may be sent as electronic, symbolic, or telephonic communications to one or more than one recipient. The nature, recipients and level of alert may be escalated based changes in the exception condition and/or failure of a recipient to respond. Further, the server may learn from past alert transmission regarding recipients and types of communications that are most effective for particular individuals, and apply this learning in further alerts.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
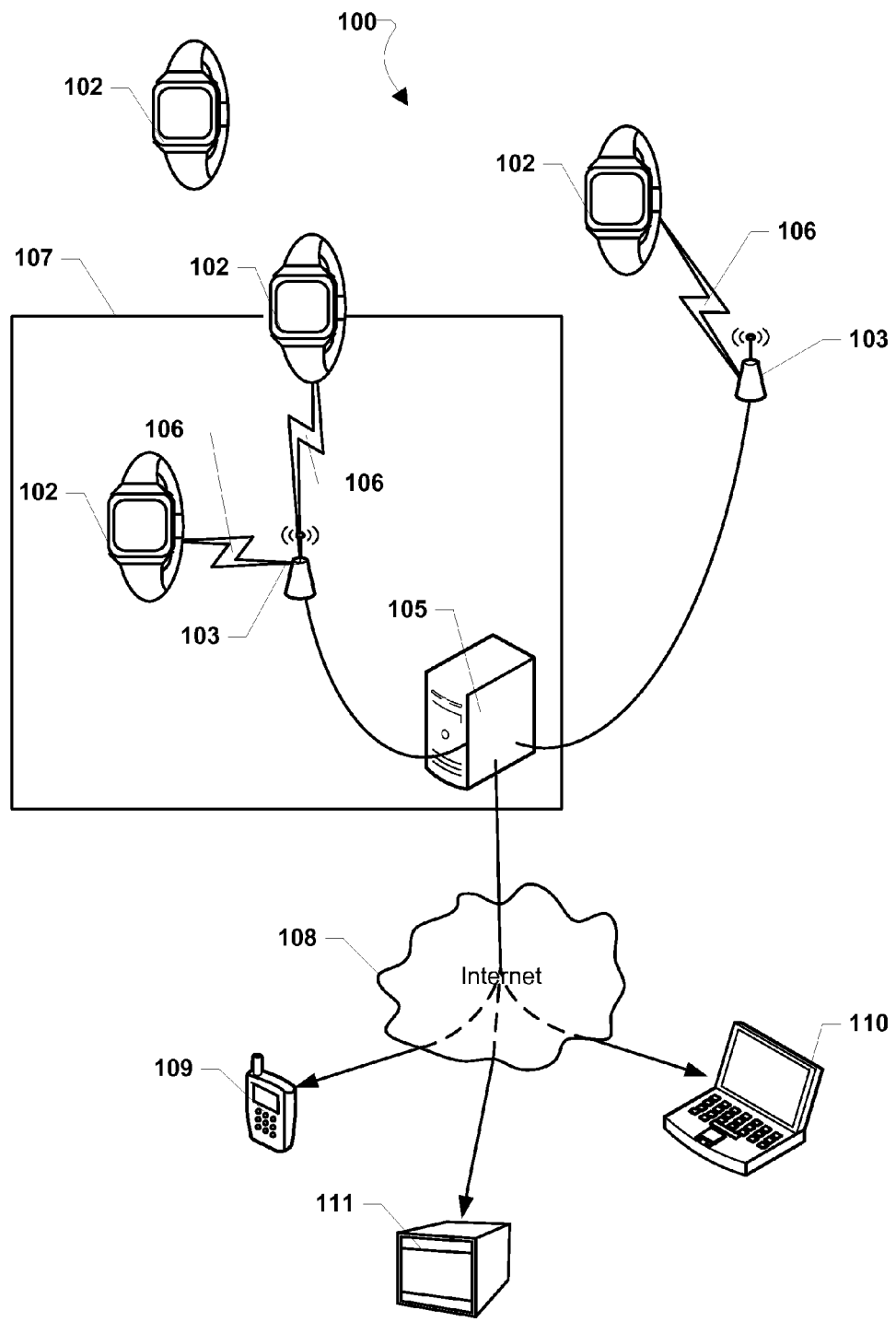
FIG. 1 is a communication system block diagram of a network suitable for use with the various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The terms "wireless mobile device" and "wireless device" are used interchangeably herein to refer to any one or all of cellular telephones, smart phones, personal or mobile multimedia players, personal data assistants (PDA's), laptop computers, tablet computers, smart books, palm-top computers, wireless electronic mail receivers, multimedia Internet enabled cellular telephones, wireless gaming controllers, and similar personal electronic devices which include a programmable processor and memory and circuitry for sending and/or receiving voice and data calls, sending and/or receiving messages (e.g., short message service (SMS) text messages, e-mails, etc.).

The term "wireless biometric sensor device" is used herein to refer to a device that may be worn or carried by a user, equipped with at least one biometric sensor, and configured to interact with a wireless communication system. In an embodiment, a wireless biometric sensor device may be configured to be worn by a user around the user's wrist in a manner similar to that of an ID tag or watch. In alternative embodiments, a wireless biometric sensor device may be in the form of a badge, tag, bracelet, patch, belt buckle, or medallion, to name but a few examples.

The various embodiments provide a system for intelligently tracking an observed population using wireless biometric sensor devices, evaluating various biometric measurements against stored information relevant to an individual, and issuing alert communications when a sensed condition indicates a likelihood of illness or injury. Examples of observed individuals wearing wireless biometric sensor devices include children attending a daycare program, students in a school, and patients within an assisted living community. The embodiments may include wireless biometric sensor devices equipped with wireless communication (e.g., Bluetooth® radios) and biometric sensing capabilities which, when affixed to an observed individual, transmit biometric sensor data via wireless signals to receiver devices, which relay the biometric sensor data to a central computing unit, such as a server. The computing unit or server may evaluate biometric data received from an individual using a biometric model. The computing unit may generate and update the biometric model by analyzing the combination of biometric parameter information collected from the observed individual over time, configured parameters, and external variables and information. When received biometric data exceeds nominal or threshold values, the computing unit may transmit an alert to notify pre-designated individuals.

The various embodiments may be implemented on a variety of computing units, such as a server, a personal computer, a work station, and a network controller when configured with processor executable instructions to perform the operations of the embodiment methods described herein. For ease of description, the various embodiments are described below referring to a server as performing the operations of the computing unit. However, the reference to servers is for illustration purposes and is not intended to limit the application to a particular type of computing unit, network architecture or implementation unless specifically recited in the claims.

Current biometric sensor data received from the individual's wireless biometric sensor device may be evaluated against the biometric model by comparing the data to nominal and/or threshold values for similar times, activities, and/or locations. In an embodiment, events and environmental variables not unique to the observed individual, such as an activities schedule or outside weather conditions, may be incorporated into the biometric model and data evaluations. The server may continually update the biometric model as the system receives biometric data, and the server may update stored values and determine logical dependencies of biometric measurements to other variables, including other biometric parameters or attributes. Using biometric models to analyze current biometric sensor data of an observed individual, the server may determine whether an exception exists that should be brought to the attention of overseeing parties, such as system operators, guardians, or other authorities. Examples of exception conditions may include abnormal sensor measurements (e.g., high body temperature and/or pulse rate), inoperable received parameters, or missing data from observed individuals. When an exception condition is recognized, the server may generate and transmit an alert notification to a pre-designated individual or individuals.

In various embodiments, the server may be configured to provide dynamic notifications of determined exception conditions. When the server concludes that current biometric sensor data received for an observed individual indicates the existence of an exception condition, the server may send an alert notification to wireless devices of overseeing parties, so they can investigate the observed individual. Examples of alert notifications may include telephonic, symbolic or electronic communications (e.g., SMS text messages, emails, or pages). Various exception conditions may have differing levels of urgency, so the server may issue alerts that depend on or are appropriate for the detected condition. For example, a determined exception indicating the potential abduction of an observed child may require a high level alert notification that is issued to many recipients (e.g., overseeing parties) using many forms of communication, while a mild fever may only require a message to a teacher, daycare attendant, or nurse.

An embodiment may enable response communications from recipients who receive alert notifications, and a server may adjust (e.g., escalate) the characteristics of alert notifications based on those responses. For example, if the server fails to receive a response from an alert notification recipient regarding a low-level alert notification, the server may send a medium-level alert notification to the same recipient. In another embodiment, the server may adjust the characteristics of alert notifications or determined exceptions based on subsequent received biometric sensor data. For example, if the server receives data indicating troubling biometric measurement changes in a persisting exception condition (e.g., a rising fever), the server may adjust the alert level and transmit a higher level alert notification regarding the exception. In an embodiment, the server may store and evaluate previous notification experiences to adjust the characteristics of an alert notification (e.g., the types of communications sent and the addresses used to send the communications). For example, the server may determine that, based on previous notifications, an alert notification recipient may respond quicker to an SMS text message alert notification than an email communication.

FIG. 1 illustrates a network system 100 suitable for use with the various embodiments. The network system 100 may include multiple devices, such as wireless biometric sensor devices 102 and wireless receiver devices 103. The wireless biometric sensor devices 102 and the wireless receiver devices 103 may exchange data via wireless signals or data links 106. As an example, the wireless data links 106 between the wireless biometric sensor devices 102 and the wireless receiver devices 103 may be Bluetooth® or other similar short-wavelength radio transmissions. As another example, the wireless data links 106 between the wireless biometric sensor devices 102 and the wireless receiver devices 103 may be WiFi transmissions, where the wireless receiver devices 103 may act as WiFi network access points (e.g., WiFi routers). Wireless receiver devices 103 may be within or outside of a structure 107. A wireless biometric sensor device 102 may transmit wireless signals 106 that may be received by the closest wireless receiver device 103 within the system 100. In another embodiment, wireless biometric sensor devices 102 may communicate with other wireless biometric sensor devices 102 which may relay transmissions to wireless receiver devices 103 in the system 100.

The wireless receiver devices 103 may include a wireless receiver circuit, such as a Bluetooth® transceiver, and a network interface configured to relay sensor data received via wireless signals to a server 105 via a network, such as the Internet 108 or a local area network. The server 105 and wireless receiver devices 103 may exchange data bi-directionally, which may enable the server 105 to employ the wireless receiver devices 103 to transmit wireless data signals to the wireless biometric sensor devices 102. Through the connection to the Internet 108, the server 105 may also exchange data with external devices capable of interacting with the Internet 108, such as a smart phone 109, a laptop 110, other servers, and a cloud data storage device 111. In this manner, communications (e.g., SMS text messages, e-mails, etc.) may be exchanged between the server 105 and other Internet-connected devices by methods well known in the art.

Wireless biometric sensor devices 102 may transmit data at pre-defined, regular intervals. For example, a wireless biometric sensor device 102 may prepare and send wireless transmissions every few seconds. The server 105 may also periodically transmit, through the wireless receiver devices 103, requests for wireless biometric sensor devices 102 to transmit data. For example, every few seconds, a scheduling application running on the server 105 may send requests to all wireless biometric sensor devices 102 receiving the wireless transmissions to respond with current measurement data communications.

In an embodiment, the system 100 may employ transmission scheduling methods to minimize wireless transmission collisions amongst the wireless biometric sensor devices 102 and wireless receiver devices 103. If numerous wireless biometric sensor devices 102 transmit data simultaneously, the resulting interference might cause incomplete or corrupted information due to radio signals arriving at the wireless receiver devices 103 simultaneously. A system's 100 transmission scheduling methods may involve assigning particular times (e.g., a time within each minute) when particular wireless biometric sensor devices 102 may exclusively transmit data to wireless receiver devices 103. For example, a particular wireless biometric sensor device 102 may be assigned a certain range of seconds within each hour to transmit to wireless receiver devices 103, during which all other wireless biometric sensor devices 102 may not transmit to the wireless receiver devices 103.

A wireless biometric sensor device 102 may transmit data messages representing biometric information about the individual using and/or wearing the wireless biometric sensor device 102. Biometric information may be measurements take from sensors located within the wireless biometric sensor device 102. Examples of such measurements may include body temperature, pulse rate, and acceleration (i.e., body motion). The data messages may include identification information about the wireless biometric sensor device 102, such as a unique ID number or code. The wireless biometric sensor device 102 may encrypt or make the data messages otherwise obscured by data security abstractions, which the server 105 may reverse through decryption techniques to make the information useable. In another embodiment, the wireless receiver devices 103 may also process data messages with encryption and/or decryption techniques.

As an illustrative example, a wireless biometric sensor device 102 having a unique identification code may include pulse rate and body temperature sensors, both being in contact with an observed individual's anatomy sufficient to produce measurements. The wireless biometric sensor device 102 may, via the sensors, determine the body temperature and pulse rate of the observed individual. The wireless biometric sensor device 102 may concatenate the temperature value, pulse rate value, and device identification code in a manner that may be parsed and understood by an associated server 105. The wireless biometric sensor device 102 may also execute a routine applying an encoding algorithm to the concatenated data, producing a data message that may be transmitted to the wireless receiver devices 103 and relayed to the server 105. When the server 105 receives the data message, the server 105 may apply decryption and parsing routines to the data message in order to produce discrete information segments representing the pulse rate, body temperature, and the identification code of the wireless biometric sensor device 102.

In an embodiment, wireless biometric sensor devices 102 may provide information about their location. Wireless receiver devices 103 may determine the location of wireless biometric sensor devices 102 through the use of ranging calculations based on data signal exchanges between the wireless receiver devices 103 and the wireless biometric sensor devices 102. In another embodiment, wireless biometric sensor devices 102 may include global positioning system (GPS) chips and report GPS coordinates via the wireless data links 106.

Data transmitted to the server 105 may include other non-biometric information, such as atmospheric conditions or physical location of an observed individual, which may be used in the evaluation of biometric, safety, or health status. For example, if an observed individual wearing a wireless biometric sensor device 102 passes a Wi-Fi hotspot (or local area network) unaffiliated with the network system 100, the wireless biometric sensor device 102 may transmit identifying characteristics of the hotspot to the server 105. As another example, if a wireless biometric sensor device 102 is equipped with a chip capable of cellular network communications (e.g., 4G LTE), the wireless biometric sensor device 102 may transmit the current cellular network data signal strength to the server 105. The server 105 may use such non-biometric information in combination with other data to extrapolate important information regarding the observed individual. For example, the server 105 may combine a frigid local atmospheric temperature measurement received from a child with a hot atmospheric temperature measurement received from an Internet weather report and determine that the child may be trapped in a freezer unit.

If wireless routing devices, such as transceiver devices 103, are employed in the delivery or direction of data to a server 105, additional information may be appended to the data originally sent by wireless biometric sensor devices 102. For example, an observed individual's wireless biometric sensor device 102 may transmit a data message that includes only its unique device identifier number and the current measurement of a body temperature sensor. The wireless receiver device 103 closest to the wireless biometric sensor device 102 may receive this data message and add its own identifying code onto the data message. Providing an identifier of the wireless receiver device 103 to a data message may enable the server 105 to determine the approximate location of the observed individual based on the known location of that wireless receiver device 103 and the communication range of wireless biometric sensor devices 102. Alternatively, a wireless receiver device 103 may append to transmitted data messages data transfer statistics, such as elapsed time between original transmissions to wireless biometric sensor devices 102 and their transmission responses to the wireless receiver devices 103. Such additional data may be used by the server 105 to troubleshoot network latency issues or even diagnose wireless biometric sensor device 102 functionality deficiencies.

The server 105 may store data it receives or generates within an electronically-stored database. If data relates to a particular observed individual, then the server 105 may store the data in the database such that it is functionally-connected to the observed individual (i.e., related database records share a unique ID key). A query may be submitted to database management software running on the server 105, from which data about the observed individual may be returned for use by the server 105. For example, a server 105 may access all the body temperature values stored after transmissions by a child's assigned wireless biometric sensor device 102.

Information within the database may be in the form of data records, which may include numeric and text data, and may be divided into numerous functionally descriptive categories. For example, a server's 105 broad query of the database for records pertaining to an observed individual ID, may return one thousand records, each consisting of numeric values for the data attributes 'time', 'date', and 'body_temperature' and a text value for attribute 'location.' As another example, a query of the database for records pertaining to that same ID but limited to the data attribute 'body_temperature' may return one thousand records consisting of only 'body_temperature' numeric values.

The information stored within the database may be a comprehensive archive of data that correspond to discrete measurements and temporal conditions (e.g., time of day, day of week, etc.). As wireless biometric sensor devices 102 transmit data to the server 105, each measurement or individual piece of information may be stored as tracked against temporal conditions (e.g., day, month, year, and time of day). For example, the database may possess countless records for a child's body temperature, one value stored for each transmission from his wireless biometric sensor device 102. The server 105 may access each record individually, and may retrieve copious records for particular time periods. In another embodiment, the database may not store each individual measurement, but instead maintain summary values in a database which evolves over time as summary values change as subsequent measurements are received by the server 105, such as a moving average. For example, instead of storing each temperature measurement in the database, the server 105 may only update and store crucial information, such as the average temperature, statistical bounds about the average temperature, and the number of total measurements received. The server 105 may save database storage space and computational costs by storing only summary information and discard individual measurements after the measurements have been evaluated against the model and the database has been updated.

The server 105 may store any information retrieved from the database in random access memory for immediate use, or alternatively, may store such information in local access storage, such as a non-volatile hard drive. To conserve space in local access storage, decrease computational costs, or minimize storage access costs, the server 105 may delimit its access to database records by only retrieving relevant subsets of information about the observed individual. For example, although the database contains stored information about a child's body temperature, pulse rate, perspiration, skin pH, and motion activity, the server 105 may only request data regarding the child's body temperature.

Figure 2:
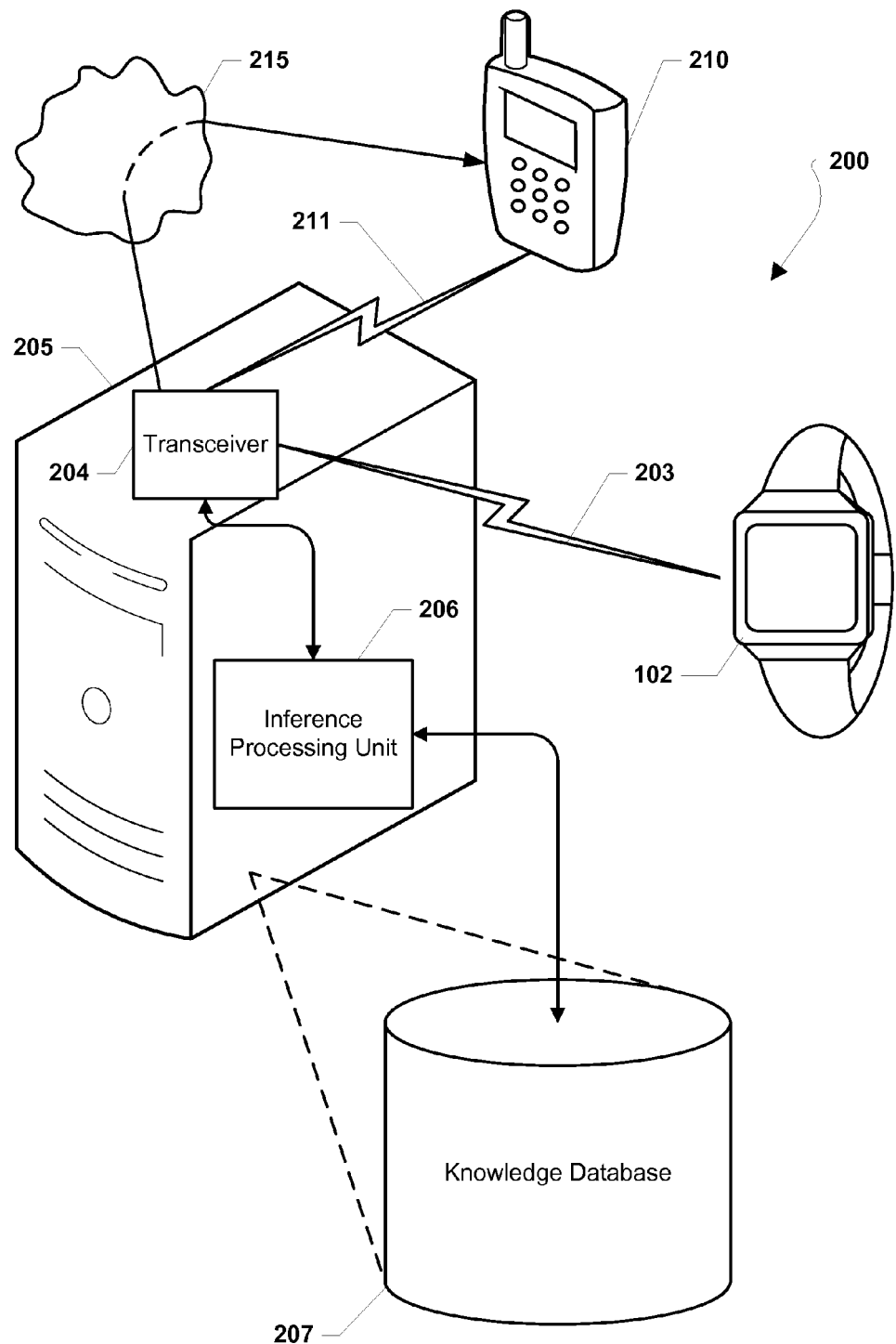
FIG. 2 is a system block diagram of a communication system suitable for use with the various embodiments.

FIG. 2. illustrates a system 200 suitable for use with the various embodiments. The system 200 may include a wireless biometric sensor device 102 worn by an individual in the observed population and a wireless device 210 accessible or carried by an individual acting in an overseeing capacity. The system 200 also may include a server, such as a server 205. In another embodiment, the server may be portable, such as a smart phone carried by an overseeing party. The wireless biometric sensor device 102 and a wireless receiver 204 associated with the server 205 may transmit data via a wireless data link 203. The wireless device 210 and the wireless receiver 204 may transmit data via another wireless data link 211, such as WiFi, or via an external communication network 215 (e.g., a cellular network). As an example, the wireless data link 203 between the wireless biometric sensor device 102 and the wireless receiver 204 may be Bluetooth®, Zigbee®, or other similar relatively short-wavelength radio receiver or transceiver.

Data sent to the server 205 by the transceiver 204 may be analyzed in an inference processing unit 206, which may be a software module implemented in the server 205. In another embodiment, the inference processing unit 206 may be a dedicated processing device within or coupled to the server 205. The inference processing unit may exchange data with the transceiver 204 in a bidirectional data flow. As an example, the wireless receiver 204 may process incoming data via wireless data link 203 from wireless biometric sensor device 102 and deliver that information to the inference processing unit 206 to be stored in memory and used to evaluate the status of an observed individual. As a further example, the inference processing unit 206 may direct an alert notification to the wireless receiver 204 and/or an external communication network 215 for wireless transmission to the wireless device 210 to alert an overseeing party.

Data received, requested and created by the server 205 may be stored and organized in the knowledge database 207 by the inference processing unit 206. The knowledge database 207 may be stored within high-capacity storage connected to the server 205. The knowledge database 207 may have the structure of a relational database and accept data originating from wireless biometric sensor device 102 measurements. The server 205 and/or the inference processing unit 206 may retrieve data from the knowledge database 207 for use in evaluating biometric information received from observed individuals. Data within the knowledge database 207 may be updated, replaced or removed based on relevant measurements, calculations and analytical determinations of the server 205 and/or the inference processing unit 206. The knowledge database 207 may be stored within local computer storage, such as in non-volatile hard drives. In another embodiment, the knowledge database 207 may be partially or fully stored within remote computer storage (e.g., "cloud" storage) that may be accessed through various Internet connections. When the knowledge database 207 is maintained in remote storage, multiple computing devices may access data pertaining to observed individuals, enabling monitoring of observed individuals at multiple installations.

In an embodiment, individuals within an observed population may be associated with or assigned to particular wireless biometric sensor devices 102. For example, while at daycare, a child may only ever wear a particular wireless biometric sensor device 102, which may be identified with a unique identification code. The identity of a wireless biometric sensor device 102 may be synonymous with the identity of an observed individual, and such associating relationships may be electronically recorded and changed within a data table. In an embodiment, the identity of the wireless biometric sensor device 102 may serve as a database query key for use while retrieving and/or updating information about an observed individual from the knowledge database 207, as described above.

Figure 3:
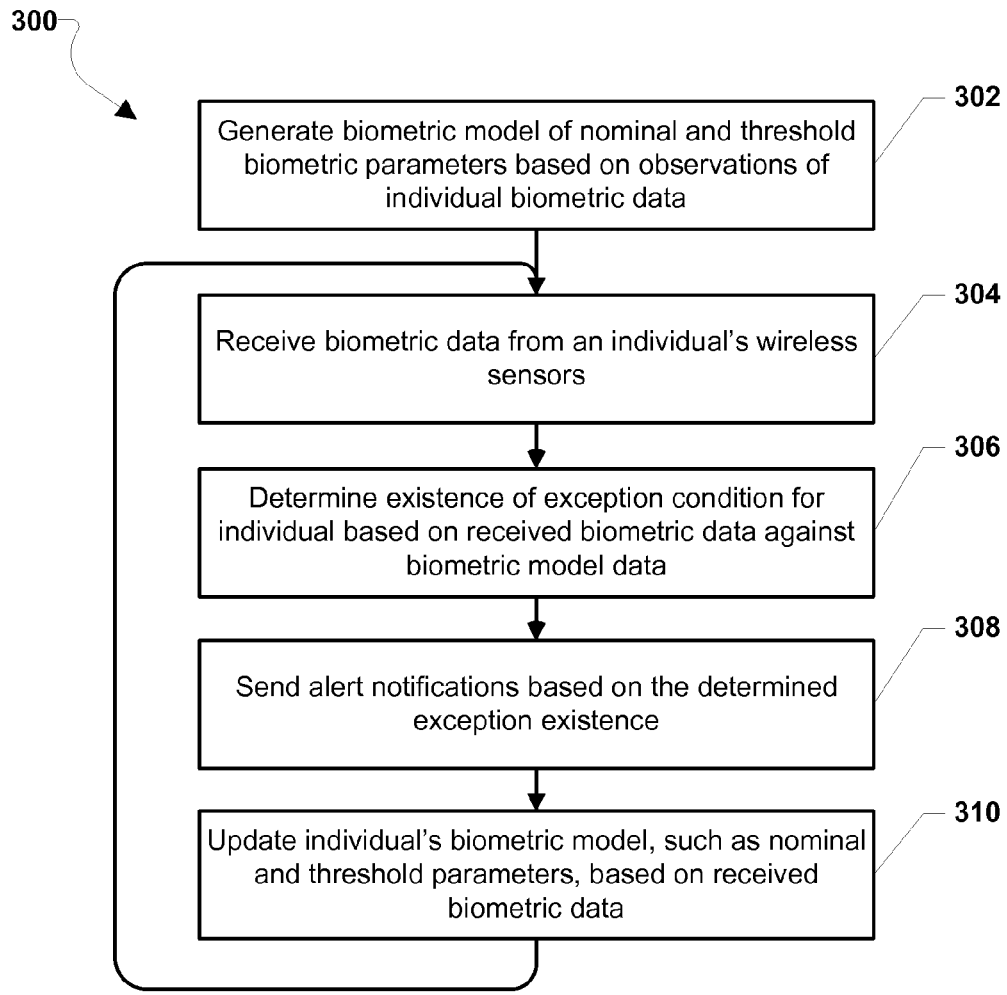
FIG. 3 is a process flow diagram illustrating an embodiment method for assessing and indicating the existence of biometric anomalies.

FIG. 3 illustrates an embodiment method 300 for a computing unit (e.g., a server) determining and acting upon exceptions based on the analysis of gathered biometric data. Over a period of time, a server implementing the embodiment method 300 may amass biometric sensor data of individuals in an observed population and derive biometric models which indicate normal biometric data values and patterns for the individuals. In an embodiment, the server may compare such biometric models against current biometric measurements of the individuals to recognize any anomalous, or exception, conditions. If an exception condition is acknowledged by the server as present or probable, the server may send notifications to overseeing parties. Any biometric measurements received may be stored and/or applied to update the biometric models for use in future determinations.

In block 302, a server may generate biometric models for individuals in an observed population based on biometric data gathered over a period of time. In an embodiment, the system, such as described above in FIG. 1, may operate in an initial state of data gathering for a period of time. During this initial data gathering period, the server may receive a significant data set of biometric sensor measurements from which it may generate a biometric model for each of the individuals in the observed population. Multiple measurements of many biometrics parameters (e.g., temperature, pulse rate, etc.) for each individual may be transmitted by wireless biometric sensor devices to the server as data messages, which may include both numeric and text content.

In block 302, the server may develop a biometric model for each observed individual by analyzing data collected from the system and represented within a database. The biometric model may be based on that individual's unique set of biometric data received from his assigned wireless biometric sensor device and configured as a benchmarking tool to be used by the server when evaluating current biometric sensor data. The biometric model, for example, may represent the nominal and threshold values of biometric attributes of the observed individual. Nominal and threshold ranges may describe the typical values for biometric attributes of the observed individual and may be used to determine if biometric measurements are anomalous (i.e., exceptions). As another example, a threshold within a biometric model for a child may be set for body temperature measurements that are a degree above or below the average body temperature for a child. Nominal and threshold ranges may be defined as a function of many factors, such as temporal conditions (e.g., time of day, day of week, day of year) and/or physical locations. For example, the nominal and threshold values for body temperature may be calculated as a function of the time of day and day of the week since a child's body temperature may change throughout the day naturally and depending on activities. In another embodiment, threshold values may be supplemented by other parameters, such as user-defined system variables stored electronically on the server. For example, a configuration file may set a threshold at two standard deviations from the mean biometric attribute value, with any measurement falling outside of this range to be determined an exception. In such an implementation, a reported temperature for a child may be recognized as an exception by the server if it is outside of two standard deviations from the calculated mean temperature for the child.

In block 302, when determining the nominal and threshold values of the biometric model of an observed individual, the server may also develop typical statistical metrics for each biometric attribute of that individual. Statistical metrics may include mean and standard deviation values for a biometric attribute. For example, the server may determine that the average and standard deviation for reported body temperatures of a child. In an embodiment, the server may store summary values of the biometric attributes, such as running averages. Statistics may also be derived using subset samples of relevant data stored in databases.

The statistical metrics may be refined by the server for specific time or date ranges to further develop the biometric model of an observed individual. For example, the server may determine the mean body temperature of a child across all times reported. However, the server may also determine the mean temperature for measurements taken during particular temporal conditions (e.g., time of day, etc.). The server may calculate a confidence assessment of any statistical determinations based on factors such as size of data set and variation of recording conditions.

The server may adjust statistical assessments described in biometric models through trend analysis. If biometric measurement values fall within the fringe of nominal parameters, the server may extrapolate any trending toward an exception. For example, if a body temperature measurement for a child is within a small amount of the exception range, the server may query stored, previous measurements for the child's temperature to discern if the child has been experiencing an increasing temperature throughout the recent past. When observing such fringe measurements, the server may determine a higher probability of an existing illness by failing to find similar progressions in the stored data. In another example, accelerometer measurements, showing a high amount of movement (or acceleration) of an observed child, may fall within average values for that child throughout the day. However, through an examination of measurements represented by the child's biometric model, the server may discern the seemingly normal accelerometer measurement to be a strong basis for an exception determination, as the activity may be occurring when the child has historically been relatively motionless.

Statistical analysis and trending may include data from the entire population as well as from the observed individual. In an instance where shallow data sets exist within the database for an observed individual, the server may reinforce statistical assumptions by supplementing normal data from other observed individuals in similar conditions. For example, during a child's first hour of daycare, the server may evaluate his measured accelerometer motion data against the average values from his entire class.

An observed individual's biometric model may be a complex data structure that relates data points to conditions that may affect the individual's biometric measurements. In an embodiment, a biometric model data structure may juxtapose normalized data ranges of measured biometric attributes, computed from information within previous individual data messages, to other factors, such as time of day, day of week, local temperature, etc. For example, the averages of a child's observed biometric attribute measurements, such as body temperature or pulse rate, may be paired with time periods corresponding to the measurements. Such a data structure may be multi-dimensional, including sets of biometric measurement ranges against N functional factors at once. For example, average value ranges for biometric attribute measurements may be in context of one factor, such as time of day, and an additional factor, such as location. Alternatively, in an embodiment the server may generate a biometric model that is the form of an algorithm in which measurements may be sequentially evaluated using factors determined from previous observations. For example, an algorithmic biometric model may evaluate a current measurement to output a probability that the individual is ill or injured, and potentially an indicator of the possible type of illness or injury.

As the server receives more observed biometric data, the server may refine the biometric model to provide better representations of nominal characteristics and exception-indicating threshold parameters. With larger data sets of biometric measurement values, computed ranges used with biometric models may become more accurate in recognizing illness or injury.

In an embodiment, the system may employ machine learning intelligence to generate and improve the biometric models based on received biometric data. The biometric model may identify connections between biometric attributes and other factors within the system that exhibit some amount of dependency. For example, new measurements for particular biometric attributes may not correspond to the biometric model's current approximation of nominal values. However, if information from the system, such as a user input, portrays the new measurements as normal, the biometric model may include a new variable or weight current biometric data for use in future evaluations of the biometric attribute. The server may draw inferences regarding causal relationships or connections between attributes and seemingly unrelated data. Based on past experiences, the biometric model may develop new dimensions within a biometric model data structure or new branches of evaluation within a biometric model algorithm.

Operations involved in block 302 may continue indefinitely or may be activated for a particular period of activity. For example, a daycare deploying an embodiment of the system may require a long period of data collection to ensure the server generates more accurate biometric models. The daycare may execute a data collection period of a month so as to experience a high amount of data as transmitted by children wearing wireless biometric sensor devices. Alternatively, the operations in block 302 may involve loading a default biometric model. For example, if an embodiment is implemented at a daycare, the system may use national averages for children of comparable age and socioeconomic characteristics as the initial default biometric model. Biometric models may be refined over time as discussed below with respect to block 310.

Continuing with FIG. 3, in block 304, the server may receive current biometric sensor data from wireless biometric sensor devices carried and/or worn by individuals in the observed population. As described above, the wireless biometric sensor devices may send data messages to the server containing information derived from biometric sensors, as well as other information, such as location coordinates. The server may receive, parse, decrypt, and associate the data with respective observed individuals.

In block 306, the server may employ generated biometric models to evaluate current biometric sensor data. As it receives current biometric measurement data from a wireless biometric sensor device, the server may compare that data to the biometric model of the respective individual to determine whether the current data represent anomalous conditions (i.e., exceptions). Exception conditions may be those which suggest physical distress, illness, or abduction of the observed individual. An embodiment of this exception existence evaluation is discussed at greater detail below with reference to FIG. 4.

In block 308, the server may transmit an alert notification based on the exception evaluations. If a comparison of the received current biometric sensor data to biometric models suggests the existence of an exception, the server may communicate with overseeing parties, via alert notification, to prompt them to investigate or remedy the exception. Embodiments of the alert notification creation and delivery operations are discussed in more detail below with reference to FIGS. 5 and 6.

Alert notifications that may be transmitted in block 308 may be of numerous forms, such as SMS texts, emails, and telephone calls with machine-generated or prerecorded verbal messages. Alert notifications may have different associated alert notification recipients or destinations for communications. Alert notification recipients and their contact information may be stored as address books, which may be described in electronic files accessible by routines running on the server. Examples of alert notification recipients may be overseeing individuals (e.g., teachers) or parents of observed individuals.

In an embodiment, alert notifications may be transmitted to the appropriate alert notification recipients by the server as data messages. The data message may be formatted by the server for delivery via email, text SMS message over a cellular network connection, or via other wireless data transmission (e.g., short range radio signal). In an embodiment, data messages may be sent via wireless transmissions from the server to wireless devices employed by alert notification recipients.

In an embodiment, alert notifications may include identifying information regarding the observed individual (e.g., wireless biometric sensor device 102 identification number) and his physical location (e.g., "outside near router #4"). The server may employ a data lookup table to find the observed individual's name and biographical details to insert into the alert notification. The alert notifications may also include the biometric attribute(s) which the server determined as causing the exception. In addition, the server may procedurally generate prose that gives intuitive descriptions of the determined exception, such as possible diagnosis and/or a summary of symptoms. For example, after determining an exception regarding a child's current high temperature, the server may generate the text "Child A has a high temperature and may be getting a cold." In another embodiment, the alert notification may include instructions regarding how the determined exception may be remedied. For example, based on the preceding example scenario, the generated text may also include "Please have Child A taken to the nurse for immediate observation." The alert notification may be further characterized by an indicator which signals whether the alert is of low, medium, or high importance. Other descriptive information may be appended to the alert notification as well, such as a unique alert notification identity code that may be used by the server in linking responses and follow up actions to alert notifications.

Returning to FIG. 3, in block 310, the server may update the biometric models using received data. The server may use the current biometric sensor data to modify the current biometric model (e.g., updating running averages), and store the updated biometric models for use in evaluating subsequent biometric data sets. Alternately or periodically, the server may use all received biometric sensor data, including the current data, to regenerate each individual's biometric model (essentially repeating the operations of block 302 including recently received biometric data). In an embodiment, block 310 operations may include adjusting nominal and threshold values used to recognize exception conditions. Such updates may refine the statistical elements of the biometric models as more biometric data are received, which may enable future exception evaluations to be more accurate. The server may make database updates by changing values within a locally stored database (e.g., in a knowledge database 207 within the server), or by transmitting data via Internet protocol communication to remote storage devices (e.g., cloud data storage device 111). In another embodiment, updating of the biometric models and other database information may occur during any operation within method 300.

Figure 4:
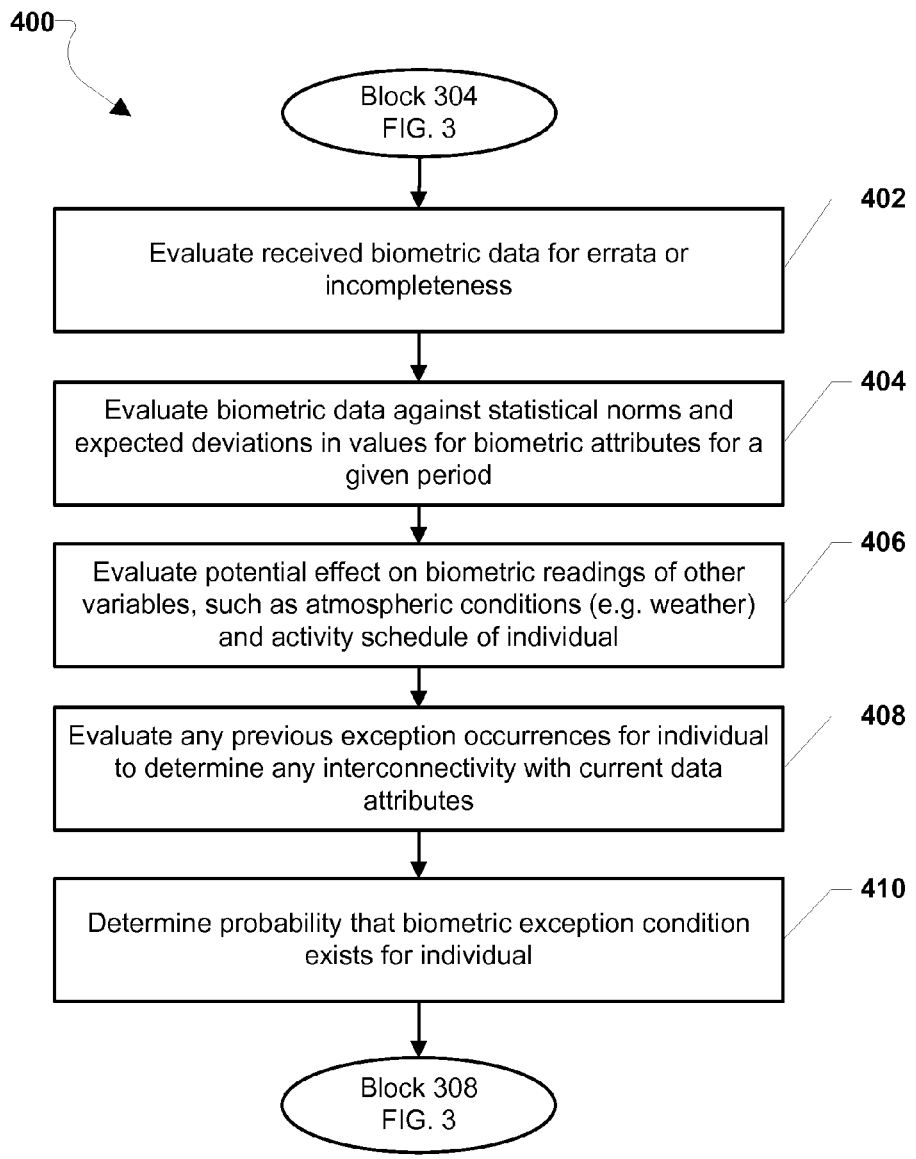
FIG. 4 is a process flow diagram illustrating an embodiment method for evaluating biometric characteristics of individuals.

FIG. 4 illustrates an embodiment method 400 for recognizing exception conditions by analyzing current biometric sensor data. The server may compare current biometric measurement data from an observed individual to the biometric model for that individual. In an embodiment, the inference processing unit may perform various distinct evaluations of data to ascertain the existence of exception conditions. Each evaluation may weigh each biometric element differently in a calculation of an exception condition or probability, and such weighting schemes may be defined within each individual's biometric model. Alternative or supplementary weighting schemes may be defined in user configuration files. The final result of an exception calculation may be a floating point numeric value that reflects a probability that the individual is ill or injured, which are referred to generally as exception conditions. For example, the inference processing unit may calculate that the current biometric measurement of a child's body temperature has a 25.5% probability of being an exception. In another embodiment, the exception evaluation may determine the existence of an exception as a binary indicator, such as 'yes' or 'no'.

In block 402, the inference processing unit may begin analyzing data received from an individual's wireless biometric sensor device. For example, the inference processing unit may determine whether the data message contains incomplete or erroneous information. In an embodiment, the inference processing unit may compare the expected types, formats and ranges of measurement data (e.g., the server requests measurements of body temperature and pulse rate) to the data actually received from wireless biometric sensor devices. For example, the server may transmit hourly commands to all wireless biometric sensor devices within the network to report, via data message, body temperature, location, and pulse rate measurements. Operations in block 402 may also detect data errors or corruption. When incomplete or grossly erroneous data are received, the inference processing unit may discard such data. The server and/or inference processing unit may also initiate a hardware maintenance request to inspect the wireless biometric sensor device which produced the incomplete data message.

In block 404, the inference processing unit may begin analyzing gathered data represented in a biometric model to determine anomalies, or exception conditions, in current biometric sensor measurements. The inference processing unit may evaluate the current biometric sensor data using expected deviations in values for biometric attributes represented in an individual's biometric model. In an embodiment, the inference processing unit may detect exception conditions if current biometric measurements do not coincide with the biometric model's threshold and nominal values for particular biometric attributes. For example, if the current measurement of a child's temperature is outside of the threshold range for normal temperatures for the child, the inference processing unit may determine an exception exists. The inference processing unit may also use statistical metrics related to the biometric model, as well as trending analysis, to evaluate current biometric measurements for exception conditions based on the biometric model data. In an embodiment, the inference processing unit may use temporal conditions (e.g., time of day, day of week, etc) and physical location of the individual to narrow the focus of the analysis of current biometric measurements against the biometric model.

In block 406 the inference processing unit may evaluate biometric data and potential exception conditions against other information that may have indirect effects on the measurement data. If a biometric attribute measurement is determined to be outside of the threshold value for an observed individual in block 404, the inference processing unit may evaluate whether there are variables that may be affecting the biometric measurement. Additional variables may be represented in the biometric model and may include, for example, location of the observed individual, atmospheric conditions (e.g., temperature, wind chill, precipitation), and scheduled activities (e.g., recess or nap time). If the inference processing unit determines such a variable is affecting an individual's biometric measurements, the inference processing unit may adjust the biometric model analysis and reevaluate the finding of an exception condition. As an example, an activities calendar, giving time, place, duration and nature of scheduled activities, may be electronically stored on a server and accessible by the inference processing unit as part of block 408. If a child's wireless biometric sensor device reports a current body temperature higher than statistical norms for similar time periods, the inference processing unit may access the schedule to determine whether the child is scheduled to be participating in a physical activity which might affect the measurement. For example, the inference processing unit may temporarily increase the threshold for body temperatures for the child during the time of the scheduled physical activity.

In an embodiment in which the inference processing unit may communicate directly or indirectly with remote servers via the Internet, the inference processing unit may also gather pertinent information from real-time third party resources as part of the operations in block 406. For example, using Internet protocol communications, the inference processing unit may request and receive atmospheric temperature data for a relevant zip code from the National Weather Service website, and use this information when evaluating an observed individual's heightened body temperature measurement.

In block 408, the inference processing unit may use previously confirmed or overruled exception conditions to analyze current biometric conditions. If any reported exceptions were confirmed or determined previously, the inference processing unit may consider such information in evaluating whether an exception condition exists. For example, if the current accelerometer data for an observed individual is within the range of previous non-exception values for a particular time, the inference processing unit may not determine a high probability of an exception existing. However, if stored data indicates an exception occurred with similar motion data and time period, the inference processing unit may modify its initial assessment to weigh biometric data more narrowly. In an embodiment, the inference processing unit may compare all current biometric attribute values to all known occurrences of exceptions in order to determine a connection or relationship amongst various biometric attributes and other conditions based on previous decisions made by overseeing parties. As an example, there may be no recorded exceptions for an individual with a certain combination of variable values (e.g., body temperature is high, body motion is active, and location is inside). However, the stored data from the database may describe that an exception was reported for the individual with only a slightly different combination of variables values (e.g., body temperature is high, body motion is active, and location is outside). The inference processing unit may determine the disjoint in the two sets of variable values and record a relationship or connection between the variables. In an embodiment, the inference processing unit may also utilize predefined attribute relationship tables that are stored, accessible, and modifiable by the server.

In block 410 the results of operations in blocks 402-408 may be combined or analyzed in unison to determine an exception condition exists. The biometric model for an individual and system settings may include weighting factors that the inference processing unit may consider in exception existence evaluations. For example, based on user configurations, the inference processing unit may not consider how biometric attributes affect one another if a biometric measurement is within one standard deviation of the mean values of all observed individuals. In another embodiment, user configurations may place more emphasis on non-biometric factors, such as class attendance rates and activity schedules, which may indicate that an illness is being passed among individuals in an observed population. For example, the inference processing unit may calculate a higher probability of an exception existing when a child is exhibiting only a nominally high body temperature, but there is currently a high absence rate in the classroom.

As described above, the exception assessment conclusion may be represented by the inference processing unit as a probability or percentage of likelihood that an exception exists. As an example, if a child has a very high reported current body temperature measurement, the inference processing unit may determine an exception existence probability of 90%.

Figure 5:
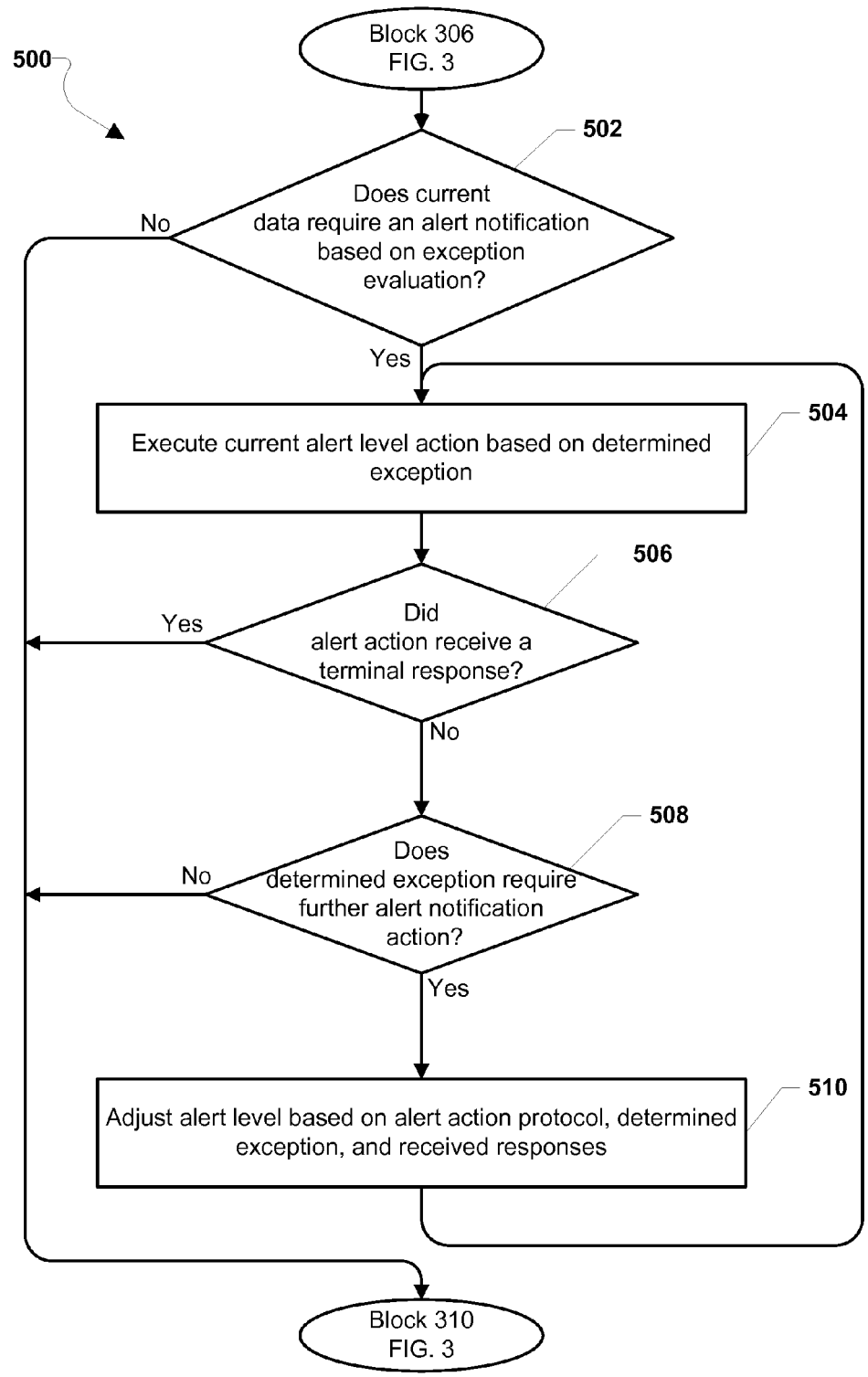
FIG. 5 is a process flow diagram illustrating an embodiment method for conducting adjusting notifications.

FIG. 5 illustrates an embodiment method 500 for creating and managing alert notifications for biometric attribute exceptions. In determination block 502, the server may determine whether an alert notification action is required based on exception existence evaluations, such as described above in respect to the embodiment in FIG. 4. The need to transmit an alert notification may be determined by comparing a floating point probability (e.g., 33%), a binary indicator (e.g., 0 or 1), or any other indicator of the existence of an exception (e.g., "strong probability") to a notification criteria or threshold. In an embodiment, the server may only determine an exception and continue with alert notification actions if exception existence evaluations are represented as affirmative binary values (i.e., '1'). If the server determines that there is no exception requiring further alert notification action (i.e., determination block 502="No"), the server may update the database and biometric model based on the biometric sensor data, as described above with reference to block 310 in FIG. 3.

In another embodiment, the server may determine an exception in determination block 502 and continue with alert notification actions if exception existence evaluations represent a minimum level of probability. For example, the server may determine an exception and pursue alert notification actions for all biometric measurements evaluated as having a 75% probability of exception. As another example, the server may determine an exception and execute alert notification actions when there is any possibility of exception existence (e.g., "some possibility" or 1% probability). Administrators of such an embodiment system may customize the level of certainty required before any exception alert notification may be transmitted in order to abate false alarms or unnecessary alert notifications. For example, a facility employing an embodiment system and having limited resources (i.e., few overseeing parties) may set a threshold level at a 75% probability of an exception existing before initiating an alert notification.

In an embodiment, the server may determine an exception using other variables, such as the biometric attributes themselves, in addition to the exception existence evaluation. The server may treat certain biometric attributes as special cases requiring alert notification action despite a lower probability of exception existence. For example, the exception existence evaluation for a child's pulse rate measurement may be determined as low probability by the server; however, the server may send alerts when there is a possibility of an exception related to pulse rate.

Returning to FIG. 5, in block 504, if the server determines that an exception alert notification should be issued (i.e., determination block 502="Yes"), the server may determine and execute actions to conduct alert notifications. The server may establish an alert level that defines the intensity or severity of the conditions regarding the determined exception. In an embodiment, the alert level may directly correspond to exception existence evaluations. For example, a "high" probability of exception determined from an exception existence evaluation may result in a 'high' alert level notification. Certain biometric attributes relating to determined exceptions may produce predefined alert levels. In an embodiment, the server may categorize any determined exception regarding certain "high concern" biometric attributes as a higher alert level and "low concern" attributes as a lower alert level. For example, if the determined exception regards a slightly elevated perspiration measurement and a corresponding high probability of exception existence, the server may classify the exception as a "low" alert level. However, if the determined exception regards an extremely low pulse rate and a lower exception existence probability, it may be a "high" or "crucial" alert level. An embodiment may enable the use of any number of alert levels. Additionally, alert levels may be gradating and sequential in nature, with low alert levels progressing in intensity to higher level alerts.

In an embodiment, specific actions may be associated with alert levels and alert action protocols may define how the server transmits alert notifications regarding the determined exceptions. Alert action protocols may encompass a number of different alert levels, each with varying associated actions, and may be stored in electronic configuration files on the server. In an embodiment, administrators of the system, such as school principals or healthcare providers, may define alert action protocols using simple programming logic. As an example: an administrator may define an alert action protocol using the code "If alert is LOW, then text J. SMITH. If alert is HIGH, call R. JONES."

In determination block 506, the server may execute a listening (or waiting) routine that awaits a response to a transmitted alert notification. The alert response listening routine may run concurrently with the normal functions of the server, persisting until the server detects a terminal response to the associated alert notification. In an embodiment, the alert response listening routine may persist for a defined duration, as may be indicated in an alert action protocol or other configuration file stored in the server. For example, administrators of the system may indicate that responses to all low level alert notifications may be terminal if accepted by the server within a day of its original transmission. If the server detects a terminal response to the alert notification (i.e., determination block 506="Yes"), then the server may update the database information with current biometric attribute measurements and any relevant information contained within the alert response (e.g., information categorizing the exception as a false alarm). An embodiment of the update operations is described above with reference to block 310 in FIG. 3.

In an embodiment, the server may maintain a data table of outstanding alert notifications which may be associated with active notification response listening routines. Outstanding alert notifications may directly correspond with a particular determined exception and may persist as outstanding until the server discontinues the listening routine associated with the particular alert notification. The server may discontinue such listening routines due to the occurrence of several events, such as a lapse of a particular time period or the receipt of a terminal response (i.e., determination block 506="Yes"). When an alert notification ceases to be outstanding, the server may remove it from the data table.

The server may use the outstanding alert notification data table when determining whether to transmit alert notifications. In an embodiment, the server may compare information from exception existence evaluations, such as described above with reference to block 306 in FIG. 3, with the outstanding alert notification data table in order to avoid executing redundant or unnecessary alert notifications. For example, the server may not acknowledge a new determined exception, and therefore not execute a new alert notification, if there is already a persisting alert notification represented in the outstanding alert notification data table that regards the same basis for the exception, including the same observed individual. This comparison by the server may preclude the transmission of redundant alert notifications.

In another embodiment, the server may query the outstanding alert notification data table and adjust alert notification characteristics due to subsequent biometric measurements related to pre-existing determined exceptions. When the server determines that received biometric sensor data corresponds to a pre-existing determined exception connected to an outstanding alert notification represented in the data table, the server may determine that the biometric sensor data is new information of an ongoing exception condition. This may occur when exception conditions persist through multiple cycles of data transmissions from the wireless biometric sensor device worn by a particular observed individual. For example, a determined exception and alert notification may exist regarding a child's elevated temperature when the server evaluates more recent biometric sensor data of showing an even higher temperature for the child. The server may interpret the more recent biometric sensor data as an update to the pre-existing determined exception and may execute a new notification based on the comparison of the characteristics of both conditions. For example, there may be a low-level, outstanding alert regarding a slightly elevated body temperature for a child in the outstanding alert notification data table. The server may subsequently evaluate biometric sensor data regarding an increased body temperature measurement for the child. Comparing the outstanding alert notification and corresponding determined exception with the subsequent biometric information, the server may cause an alert level escalation and transmit a new alert notification of heightened intensity or severity.

In an embodiment, the server may define responses as received communications that contain pairing information for an outstanding alert notification. For example, if the server receives an electronic text communication regarding a determined exception having a unique code, the server may deem the communication a response to that exception's outstanding alert notification. A terminal response may be a response received by the server that indicates that the server may discontinue the listening routine associated with a particular alert notification. Using the immediately preceding example, the server may interpret a response regarding the determined exception's outstanding alert notification as terminal if the response indicates that the exception has been resolved. In another embodiment, all responses received by the server may be terminal responses for their respective alert notifications.

Alert notification responses may be in the form of direct input to the server (e.g., a mouse click or keyboard entry command), data messages transmitted from an alert notification recipient, or any other electronic communication sent by an alert notification recipient and received by the server. For example, an alert notification recipient, receiving an alert notification regarding a determined exception on his smart phone, may click a graphical user interface button shown on the phone's display unit which initiates a wireless data message transmission to the server and which the server may interpret as a response regarding the exception. Alert notification responses may contain information which may function as commands to the server. In an embodiment, responses may be sent by recipients which may direct the server to continue or discontinue a particular response listening routine, validate a determined exception, change an alert level, modify an alert notification action for a determined exception, or update information accessible by the server, such as data stored in a database. For example, the recipient described in the above example may click a 'Disregard' button on his smart phone after having received the alert notification, causing the smart phone to send a data message to the server, which interprets the data message as a command to discontinue the listening routine corresponding to the exception. As another example, the recipient may instead click a button 'Escalate' in response to an alert notification, which may be interpreted by the server as a command to increase the alert level of the exception.

Returning to FIG. 5, in determination block 508, when the server does not detect a terminal response (i.e., determination block 506="No"), the server may decide whether to continue the alert notification process by conducting further alert notification actions. The server may base this decision on factors including non-terminal alert notification response information (e.g., a response instructs the server to increase the alert level) and determined exception characteristics (e.g., the condition relates to a high concern biometric attribute). For example, the server may proceed with the alert notification process if a received alert notification response indicates that the alert level for a determined exception should be increased. If the server determines no further alert notification action or adjustment is required (i.e., determination block 508="No"), the server may conduct an update operation, as described above with reference to block 310 in FIG. 3.

In an embodiment, the server may decide to continue with the alert process if the current alert is of a particular level. For example, the server may proceed with the alert notification process when there is no response to an alert notification of at least a medium alert level. In another embodiment, the server may determine that further alert notifications are unnecessary when the exception regards less essential attributes, such as skin pH. In determination block 508, the server may make its determination using other circumstantial factors as well, including the number of alert notifications and alert level adjustments already conducted for a particular determined exception. For example, the server may determine that an exception regarding a slight temperature of a child may not require further alert notifications after two notifications were sent in the recent time period.

In another embodiment, administrators of the system may define contingency actions (e.g., alert action protocols) which influence how the server will proceed in determination block 508. For example, an administrator may define a contingency action appended to an alert action protocol, such as "If alert is LOW, then text J. SMITH. If no response, then QUIT." Such alert action protocols may contain counters as well, which may dictate how many notifications should be sent for each alert level, action, or determined exception. For example, an alert action protocol may contain, "If alert is LOW, then text J. SMITH. If no response, then RETRY 3 times."

In block 510, when the server does not receive a terminal response to an alert notification but continues to conduct the alert notification process (i.e., determination block 508="Yes"), the server may adjust the alert level of a determined exception to represent a different importance or urgency. In an embodiment, the server may represent an alert level adjustment by modifying a system variable engendering the alert level. The server may continue to adjust alert levels (e.g., lower, escalate) and execute alert notification actions based on the adjusted levels, as described above with reference to block 504.

In an embodiment, in block 510 the server may utilize gradated alert action protocols with which each successive alert level encompasses intensified alert notification actions. For example, a first, low alert level may cause the server to transmit a single SMS text message alert notification to an alert notification recipient (e.g., an on-site guardian), encouraging the alert notification recipient to investigate the exception condition. The next, medium alert level may cause the server to transmit another alert notification via SMS text message to the same alert notification recipient, demanding the person to investigate the probable exception case. The medium alert level may involve the server sending additional SMS text messages to more alert notification recipients associated with the alert level (e.g., parents). The high alert level may cause the server to send "EMERGENCY" SMS text alert notifications to all alert notification recipients, including emergency services (e.g., the fire department).

Figure 6:
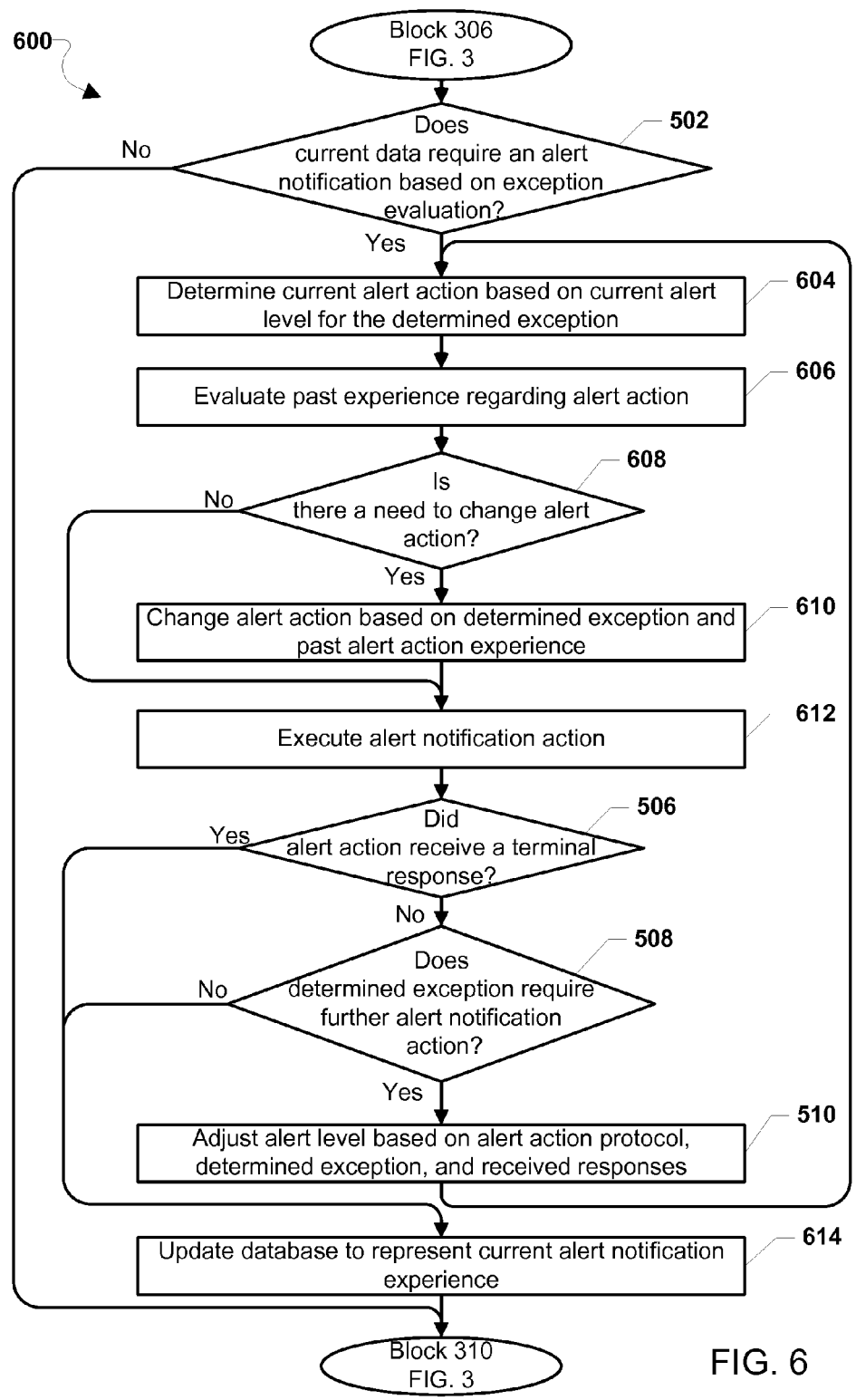
FIG. 6 is a process flow diagram illustrating an embodiment method for conducting adjusting notifications using previous experiences.

FIG. 6 illustrates another embodiment method 600 for managing alert notifications for biometric attribute exceptions. In this embodiment, the server may incorporate machine learning techniques to modify alert notifications based on notification responses. In determination block 502, the server may determine exceptions, as described above with reference to FIG. 5. If no exceptions are detected (i.e., determination block 502="No"), the server may proceed to an update operation, as described above in block 310 in FIG. 3. If the server determines an exception (i.e., determination block 502="Yes"), in block 604 the server may establish alert levels and corresponding alert notification actions based on the determined exception, such as described above with reference to block 504 in FIG. 5. However, unlike the operations in block 504, these actions may be prescribed but not executed by the server.

In block 606, the server may evaluate the prescribed but unexecuted alert notification actions by comparing these actions to experiences of previously executed actions. Previous alert notification experiences may be stored in a database as described below with reference to block 614. Using the database information, the server may determine expected responses based on previous response performances of similar notification characteristics. For example, if the prescribed mid-level alert notification action for the determined exception warrants an SMS text message, the server may determine the expected response time as the average response time for all previous SMS text messages. In an embodiment, the server may also analyze alert notification recipients associated with the prescribed alert notification action and evaluate their previous responses to similar circumstances. For example, the server may determine a recipient's expected response time for a low-level alert notification based on the recipient's previous responses to similar messages.

In determination block 608, the server may decide if it needs to change the prescribed alert notification action based on the evaluations described in block 606. If prescribed alert notification actions are inadequate for a determined exception (i.e., the expected response time is too long), then the server may need to change those actions. In an embodiment, the server may evaluate the adequacy of the expected responses to the prescribed alert notification action using the characteristics of the determined exception, such as the alert level. For example, the server may determine that the prescribed SMS text message alert notification is inadequate for a high alert level exception because the expected response time is several hours. As another example, the server may determine that the prescribed SMS text message alert notification is adequate for a low alert level exception as previous similar exceptions for the observed individual have resolved without any responses. In an embodiment, the server may use thresholds values stored within data tables to evaluate the adequacy of the expected response time for prescribed alert notification actions. For example, the server may compare the expected response time of a prescribed low-level alert notification to a data table which lists acceptable response times for each alert level. If the expected response is within the data table's threshold of acceptable response times for low level alerts, then the server may deem the prescribed alert notification action adequate for execution regarding the particular determined exception. In an embodiment, the data table may be multi-dimensional and provide response time thresholds based on many variables, such as alert level and message type. In another embodiment, the server may adjust acceptable response time data table values based on notification experiences. If the server determines the prescribed alert notification action is adequate for the exception and does not need to be changed (i.e., determination block 608="No"), the server may execute the prescribed alert notification action in block 612.

In block 610, the server may use the stored previous experience information to modify the prescribed alert notification actions when the action requires change (i.e., determination block 608="Yes"). In an embodiment, the server may use previous response time values (e.g., averages) to augment listening durations indicated in alert action protocols. For example, over the course of many alert notifications, an alert notification recipient's average time to respond to email notification may be only three minutes; therefore, the server may change the prescribed alert notification action to wait for email responses from that recipient for up to three minutes instead of ten minutes. The server may also adjust alert notification actions based on the data tables of threshold values as described above with reference to determination block 608. For example, the server may change a prescribed alert notification action to wait for responses only as long as the wait period falls within the threshold for a certain alert level. In an embodiment, a lack of responses to a particular alert notification action may be recognized by the server, which may replace the unsuccessful action with an alternative. For example, if a recipient has consistently failed to respond to email alert notifications, the server may instead attempt to contact the recipient via SMS text message. In an embodiment, the server may change the alert notification recipient, transmission method, or any other characteristic of a prescribed alert notification action.

In block 612, the server may execute the alert notification action established by the operations described in blocks 604-610. The execution of alert notification actions, such as the transmission of SMS text messages via the server, is described above with reference to block 504 in FIG. 5. The server may also detect the receipt of terminal responses to alert notifications in determination block 506, determine if further actions are required for particular alert notifications in determination block 508, adjust alert levels in block 510, and continue the method 600. The operations in determination blocks 506 and 508 and block 510 are as described above with reference to FIG. 5.

In block 614, when there is a terminal response (i.e., determination block 506="Yes") or if no further response is required (i.e., determination block 508="No"), the server may store within a database specific information regarding a response to the alert notification. In relation to received responses, the server may store characteristics of the alert notification, such as the alert level, identity of the observed individual, and the corresponding determined exception. In an embodiment, alert notification characteristics may include a determination of whether the alert level of the notification was escalated or otherwise adjusted from its original alert level. The server may also store information whether or not a response was received for a particular alert notification. In an embodiment, the server may store response times by various recipients (i.e., overseeing parties) for various alert notification characteristics. For example, the server may record that an alert notification recipient took an hour to respond to a low-level alert regarding a body temperature exception. The server may store and/or update summary calculations (e.g., running averages) for response times by particular alert notification recipients based on various alert notification characteristics. For example, the database may contain a running average of the response times by an alert notification recipient regarding email alert notifications. In another embodiment, the server may also track and store combinations of factors, such as notification transmission type and alert notification recipient identities, that have resulted in particular responses. For example, the server may determine that an alert notification recipient responds quickly to SMS text message notifications, and so may record the combination. When there are no alert notification actions or decisions to execute, the server may proceed to update operations, such as described above with reference to block 310 in FIG. 3.

Figure 7:
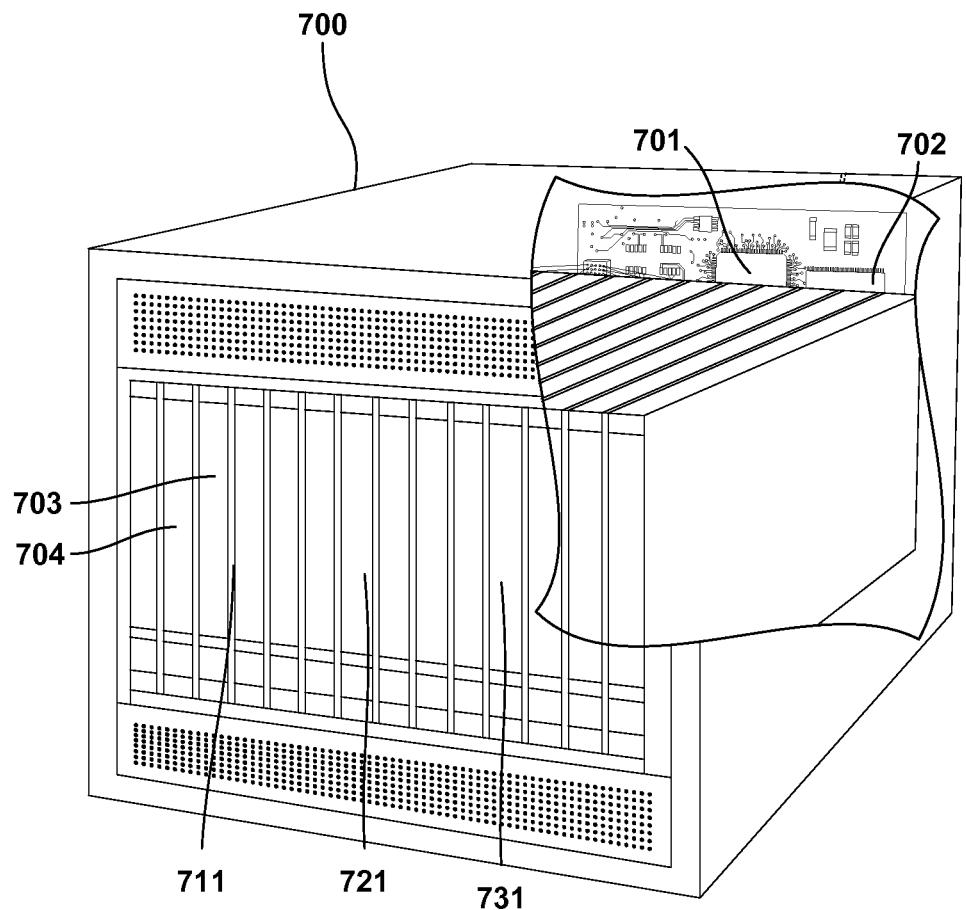
FIG. 7 is a component block diagram of a server computing device suitable for use with the various embodiments.

The computing unit used in the various embodiments may be any of a variety of commercially available server devices, such as the server 700 illustrated in FIG. 7. Such a server 700 typically includes a processor 701, and may include multiple processor systems 711, 721, 731, one or more of which may be or include multi-core processors. The processor 701 may be coupled to volatile memory 702 and a large capacity non-volatile memory, such as a disk drive 703. The server 700 may also include a floppy disc drive, compact disc (CD) or DVD disc drive coupled to the processor 701. The server 700 may also include network access ports 704 coupled to the processor 701 for establishing data connections with a network, such as a local area network coupled to other broadcast system computers and servers.

Figure 8:
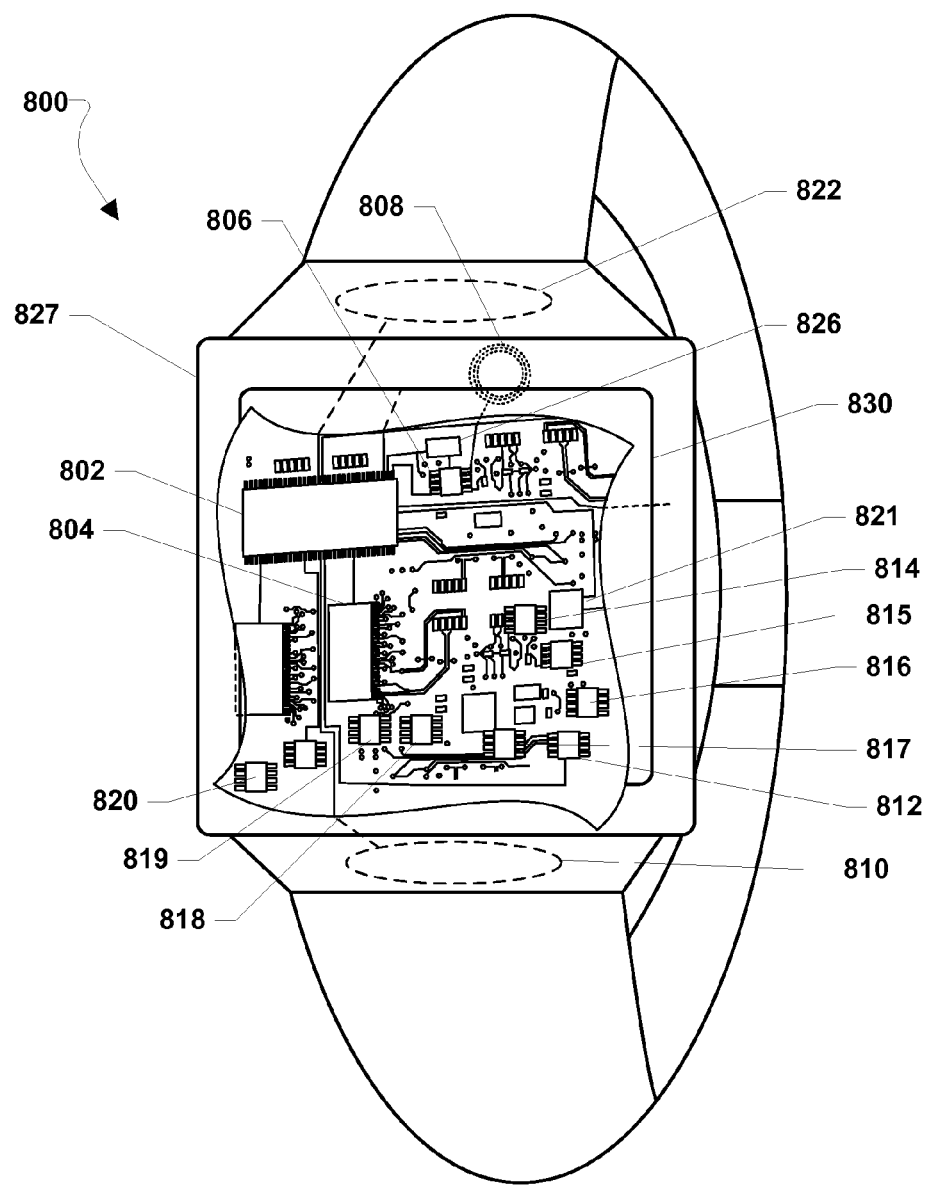
FIG. 8 is a component diagram of a wireless biometric sensor device suitable for use with the various embodiments.

The various embodiments described above may also be implemented within a variety of wireless biometric sensor devices, such as a wrist watch-type wireless biometric sensor device 800 as illustrated in FIG. 8. The wireless biometric sensor device 800 may include a processor 802 coupled to an internal memory 804. Internal memory 804 may be volatile or non-volatile memory, and may also be secure and/or encrypted memory, or unsecure and/or unencrypted memory, or any combination thereof. The processor 802 may also be coupled to a touch screen display 830, such as a resistive-sensing touch screen, capacitive-sensing touch screen infrared sensing touch screen, or the like. Additionally, the wireless biometric sensor device 800 may include a short-range radio signal transceiver 806 (e.g., a Bluetooth®, Zigbee®, or Peanut® radio) and an antenna 808 for sending and receiving wireless transmissions described herein. The wireless biometric sensor device 800 may also include physical buttons 822 and 810 for receiving user inputs. The wireless biometric sensor device 800 may also include a vibratory motor 821 coupled to the processor 802 to enable the wireless biometric sensor device 800 to vibrate. The wireless biometric sensor device 800 may also include various sensors, such as a body temperature sensor 814, a pH sensor 815, a perspiration sensor 816, a blood pressure sensor 817, a pulse rate sensor 818, a blood sugar level sensor 819, a blood oxygen level sensor 820, and an accelerometer 812 coupled to the processor 802. The wireless biometric sensor device 800 may include a battery 826.

The sensors 814-820 may require sufficient contact with the individual using the wireless biometric sensor device 800 to enable biometric measurements. In an embodiment, sensors 814-820 may be permanently positioned within the surface of the wireless biometric sensor device casing 827. In another embodiment, sensors 814-820 may be removable units tethered to the wireless biometric sensor device 800 with cable capable of enclosing and providing digital information transmission. As an example, sensors 814-820 may be units extracted from the wireless biometric sensor device casing 827, connected to the functional circuitry of the wireless biometric sensor device through fiber optic cables, and affixed to the user's skin using adhesive.

The processors 701, 711, 721, 731, 802 may be any programmable microprocessor, microcomputer or multiple processor chip or chips that can be configured by software instructions (applications) to perform a variety of functions, including the functions of the various embodiments described above. In some devices, multiple processors may be provided, such as one processor dedicated to wireless communication functions and one processor dedicated to running other applications. Typically, software applications may be stored in the internal memory 702, 804 before they are accessed and loaded into the processors 701, 711, 721, 731, 802. The processors 701, 711, 721, 731, 802 may include internal memory sufficient to store the application software instructions. In many devices the internal memory may be a volatile or non-volatile memory, such as flash memory, or a mixture of both. For the purposes of this description, a general reference to memory refers to memory accessible by the processors 701, 711, 721, 731, 802 including internal memory or removable memory plugged into the wireless biometric sensor device and memory within the processors 701, 711, 721, 731, 802 themselves.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The operations of a method or algorithm disclosed herein may be embodied in a server or processor-executable software module which may reside on a tangible, non-transitory computer-readable storage medium. Tangible, non-transitory computer-readable storage media may be any available media that can be accessed by a computer (e.g., a server). By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or server processor-executable instructions on a non-transitory machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method of monitoring a population of individuals for health and safety, comprising:
    generating a biometric model of nominal and threshold biometric parameters for each individual of the population based on biometric sensor data obtained by one or more biometric sensors and transmitted wirelessly from a plurality of wireless biometric sensor devices which are connected to the sensors and carried by the individuals of the population;
    receiving, at a server, current biometric sensor data from the plurality of wireless biometric sensor devices;
    associating, in the server, the current biometric sensor data received from each of the plurality of mobile devices with a respective individual;
    evaluating the current biometric sensor data for the individual using the biometric model for that individual;
    determining an exception condition when the current biometric sensor data is outside of a nominal range of at least one biometric parameter for the individual;
    transmitting an alert notification in response to determining the exception condition; and
    updating the biometric model for the individual based on the current biometric sensor data,
    wherein the biometric model for each individual is determined by the server analyzing received biometric sensor data for each individual over a period of time to calculate average and threshold values for each biometric parameter as a function of physical location of each individual.

2. The method of claim 1, wherein the biometric model for each individual is determined by the server analyzing received biometric sensor data for each individual over a period of time to calculate average and threshold values for each biometric parameter as a function of temporal conditions.

3. The method of claim 2, further comprising:
    determining temporal conditions at the time the current biometric sensor data is to the server,
    wherein evaluating the current biometric sensor data for the individual using the biometric model for that individual comprises comparing the current biometric sensor data for the individual to nominal ranges of the biometric parameters for that individual in temporal conditions similar to those of the temporal conditions at the time the current biometric sensor data is transmitted to the server.

4. The method of claim 1, wherein the biometric model for each individual is determined by the server analyzing received biometric sensor data for each individual over a period of time to calculate average and threshold values for each biometric parameter as a function of scheduled activities.

5. The method of claim 4, further comprising:
    determining scheduled activities for the population of individuals at the time the current biometric sensor data is transmitted to the server, wherein evaluating the current biometric sensor data for the individual using the biometric model for that individual comprises comparing the current biometric sensor data for the individual to nominal ranges of the biometric parameters during activities similar to the scheduled activities at the time the current biometric sensor data is transmitted to the server.

6. The method of claim 1, wherein the biometric model for each individual is determined by the server analyzing received biometric sensor data for each individual over a period of time to calculate average and threshold values for each biometric parameter as a function of atmospheric conditions.

7. The method of claim 6, further comprising:
determining the atmospheric conditions for the population of individuals at the time the current biometric sensor data is transmitted to the server,
wherein evaluating the current biometric sensor data for the individual using the biometric model for that individual comprises comparing the current biometric sensor data for the individual to nominal ranges of the biometric parameters for that individual in atmospheric conditions similar to those of the atmospheric conditions at the time the current biometric sensor data is transmitted to the server.

8. The method of claim 1, further comprising:
determining the physical location of the individuals in the population at the time the current biometric sensor data is transmitted to the server,
wherein evaluating the current biometric sensor data for each respective individual using the biometric model for that individual comprises comparing the current biometric sensor data for each respective individual to nominal ranges of the biometric parameters for that individual while at the physical location at the time the current biometric sensor data is transmitted to the server.

9. The method of claim 1, wherein the biometric model for each individual is determined by the server analyzing received biometric sensor data for each individual over a period of time to identify dependencies between various biometric parameters.

10. The method of claim 1, wherein updating the biometric model for the individual comprises adjusting nominal and threshold values to represent the current biometric sensor data.

11. The method of claim 1, wherein updating the biometric model for the individual comprises adjusting nominal and threshold values to represent information arising from responses to alert notifications.

12. The method of claim 1, further comprising determining an exception condition based upon determining that the current biometric sensor data describes biometric measurements that are outside a nominal range of a biometric parameter in a manner that suggests illness or injury.

13. The method of claim 1, wherein the alert notification is determined by characteristics of the exception condition.

14. The method of claim 1, wherein transmitting the alert notification comprises sending one of electronic, symbolic, or telephonic communications.

15. The method of claim 1, wherein transmitting the alert notification comprises sending communications to more than one recipient.

16. The method of claim 1, further comprising transmitting additional alert notifications in response to adjustments of alert levels based upon changes in the exception condition.

17. The method of claim 1, wherein the alert notification is determined by evaluating responses to previous alert notifications transmitted in response to previous exception conditions similar to the exception condition.

18. The method of claim 1, wherein the biometric parameters measured by the one or more biometric sensors is one or more of temperature, acceleration, pulse rate, blood pressure, blood oxygen level, blood sugar level, pH of skin, and presence of perspiration.

19. A server, comprising:
a memory; and
a server processor coupled to the memory and configured with server processor-executable instructions to perform operations comprising:
generating a biometric model of nominal and threshold biometric parameters for each individual of a population based on biometric sensor data obtained from a plurality of wireless biometric sensor devices which are attached to the individuals of the population and comprise one or more biometric sensors;
receiving current biometric sensor data from the plurality of wireless biometric sensor devices;
associating the current biometric sensor data received from each mobile device with a respective individual;
evaluating the current biometric sensor data for the individual using the biometric model for that individual;
determining an exception condition when the current biometric sensor data is outside of a nominal range of at least one biometric parameter for the individual;
transmitting an alert notification in response to determining the exception condition; and
updating the biometric model for the individual based on the current biometric sensor data,
wherein generating the biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of physical location of each individual.

20. The server of claim 19, wherein the server processor is configured with server processor-executable instructions to perform operations such that generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of temporal conditions.

21. The server of claim 20, wherein:
the server processor is configured with server processor-executable instructions to perform operations further comprising determining temporal conditions at the time the current biometric sensor data is transmitted to the server; and
the server processor is configured with server processor-executable instructions such that evaluating the current biometric sensor data for the individual using the biometric model for that individual comprises comparing the current biometric sensor data for the individual to nominal ranges of the biometric parameters for that individual in temporal conditions similar to those of the temporal conditions at the time the current biometric sensor data is transmitted to the server.

22. The server of claim 19, wherein the server processor is configured with server processor-executable instructions to perform operations such that generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of scheduled activities.

23. The server of claim 22, wherein:
the server processor is configured with server processor-executable instructions to perform operations further comprising determining scheduled activities for the population of individuals at the time the current biometric sensor data is transmitted to the server; and
the server processor is configured with server processor-executable instructions such that evaluating the current biometric sensor data for the individual using the biometric model for that individual comprises comparing the current biometric sensor data for the individual to nominal ranges of the biometric parameters during activities similar to the scheduled activities at the time the current biometric sensor data is transmitted to the server.

24. The server of claim 19, wherein the server processor is configured with server processor-executable instructions to perform operations such that generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of atmospheric conditions.

25. The server of claim 24, wherein:
the server processor is configured with server processor-executable instructions to perform operations further comprising determining the atmospheric conditions for the population of individuals at the time the current biometric sensor data is transmitted to the server; and
the server processor is configured with server processor-executable instructions such that evaluating the current biometric sensor data for the individual using the biometric model for that individual comprises comparing the current biometric sensor data for the individual to nominal ranges of the biometric parameters for that individual in atmospheric conditions similar to those of the atmospheric conditions at the time the current biometric sensor data is transmitted to the server.

26. The server of claim 19, wherein:
the server processor is configured with server processor-executable instructions to perform operations further comprising determining the physical location of the individuals in the population at the time the current biometric sensor data is transmitted to the server; and
the server processor is configured with server processor-executable instructions such that evaluating the current biometric sensor data for each respective individual using the biometric model for that individual comprises comparing the current biometric sensor data for each respective individual to nominal ranges of the biometric parameters for that individual while at the physical location at the time the current biometric sensor data is transmitted to the server.

27. The server of claim 19, wherein the server processor is configured with server processor-executable instructions to perform operations such that generating a biometric model of nominal and threshold biometric parameters for each individual of a population based on biometric sensor data obtained from a plurality of wireless biometric sensor devices comprises analyzing received biometric sensor data for each individual over a period of time to identify dependencies between various biometric parameters.

28. The server of claim 19, wherein the server processor is configured with server processor-executable instructions such that updating the biometric model for the individual comprises adjusting nominal and threshold values to represent the current biometric sensor data.

29. The server of claim 19, wherein the server processor is configured with server processor-executable instructions such that updating the biometric model for the individual comprises adjusting nominal and threshold values to represent information arising from responses to alert notifications.

30. The server of claim 19, wherein the server processor is configured with server processor-executable instructions to perform operations further comprising determining an exception condition based upon determining that the current biometric sensor data describes biometric measurements that are outside a nominal range of a biometric parameter in a manner that suggests illness or injury.

31. The server of claim 19, wherein the server processor is configured with server processor-executable instructions to perform operations further comprising determining the alert notification for transmission based on characteristics of the exception condition.

32. The server of claim 19, wherein the server processor is configured with server processor-executable instructions such that transmitting an alert notification in response to determining the exception condition comprises sending one of electronic, symbolic, or telephonic communications.

33. The server of claim 19, wherein the server processor is configured with server processor-executable instructions such that transmitting an alert notification in response to determining the exception condition comprises sending communications to more than one recipient.

34. The server of claim 19, wherein the server processor is configured with server processor-executable instructions to perform operations further comprising transmitting additional alert notifications in response to adjustments of alert levels based upon changes in the exception condition.

35. The server of claim 19, wherein the server processor is configured with server processor-executable instructions to perform operations further comprising determining the alert notification for transmission by evaluating responses to previous alert notifications transmitted in response to previous exception conditions similar to the exception condition.

36. The server of claim 19, wherein the server processor is configured with server processor-executable instructions to perform operations such that the biometric sensor data evaluated and used in updating the biometric model comprises one or more of temperature, acceleration, pulse rate, blood pressure, blood oxygen level, blood sugar level, pH of skin, and presence of perspiration.

37. A server, comprising:
means for generating a biometric model of nominal and threshold biometric parameters for each individual of a population based on biometric sensor data obtained from a plurality of wireless biometric sensor devices which are attached to the individuals of the population and comprise one or more biometric sensors;
means for receiving current biometric sensor data from the plurality of wireless biometric sensor devices;
means for associating the current biometric sensor data received from each mobile device with a respective individual;

means for evaluating the current biometric sensor data for the individual using the biometric model for that individual;

means for determining an exception condition when the current biometric sensor data is outside of a nominal range of at least one biometric parameter for the individual;

means for transmitting an alert notification in response to determining the exception condition; and means for updating the biometric model for the individual based on the current biometric sensor data, wherein the means for generating a biometric model of nominal and threshold biometric parameters for each individual of a population based on biometric sensor data obtained from a plurality of wireless biometric sensor devices comprises means for analyzing received biometric sensor data for each individual over a period of time to calculate average and threshold values for each biometric parameter as a function of physical location of each individual.

38. The server of claim 37, wherein means for generating a biometric model of nominal and threshold biometric parameters for each individual of a population based on biometric sensor data obtained from a plurality of wireless biometric sensor devices comprises means for analyzing received biometric sensor data for each individual over a period of time to calculate average and threshold values for each biometric parameter as a function of temporal conditions.

39. The server of claim 38, further comprising means for determining temporal conditions at the time the current biometric sensor data is transmitted to the server, wherein means for evaluating the current biometric sensor data for the individual using the biometric model for that individual comprises means for comparing the current biometric sensor data for the individual to nominal ranges of the biometric parameters for that individual in temporal conditions similar to those of the temporal conditions at the time the current biometric sensor data is transmitted to the server.

40. The server of claim 37, wherein means for generating a biometric model of nominal and threshold biometric parameters for each individual of a population based on biometric sensor data obtained from a plurality of wireless biometric sensor devices comprises means for analyzing received biometric sensor data for each individual over a period of time to calculate average and threshold values for each biometric parameter as a function of scheduled activities.

41. The server of claim 40, further comprising means for determining scheduled activities for the population of individuals at the time the current biometric sensor data is transmitted to the server, wherein means for evaluating the current biometric sensor data for the individual using the biometric model for that individual comprises means for comparing the current biometric sensor data for the individual to nominal ranges of the biometric parameters during activities similar to the scheduled activities at the time the current biometric sensor data is transmitted to the server.

42. The server of claim 37, wherein means for generating a biometric model of nominal and threshold biometric parameters for each individual of a population based on biometric sensor data obtained from a plurality of wireless biometric sensor devices comprises means for analyzing received biometric sensor data for each individual over a period of time to calculate average and threshold values for each biometric parameter as a function of atmospheric conditions.

43. The server of claim 42, further comprising means for determining the atmospheric conditions for the population of individuals at the time the current biometric sensor data is transmitted to the server, wherein means for evaluating the current biometric sensor data for the individual using the biometric model for that individual comprises means for comparing the current biometric sensor data for the individual to nominal ranges of the biometric parameters for that individual in atmospheric conditions similar to those of the atmospheric conditions at the time the current biometric sensor data is transmitted to the server.

44. The server of claim 37, further comprising means for determining the physical location of the individuals in the population at the time the current biometric sensor data is transmitted to the server, wherein means for evaluating the current biometric sensor data for each respective individual using the biometric model for that individual comprises means for comparing the current biometric sensor data for each respective individual to nominal ranges of the biometric parameters for that individual while at the physical location at the time the current biometric sensor data is transmitted to the server.

45. The server of claim 37, wherein means for generating a biometric model of nominal and threshold biometric parameters for each individual of a population based on biometric sensor data obtained from a plurality of wireless biometric sensor devices comprises means for analyzing received biometric sensor data for each individual over a period of time to identify dependencies between various biometric parameters.

46. The server of claim 37, wherein means for updating the biometric model for the individual comprises means for adjusting nominal and threshold values to represent the current biometric sensor data.

47. The server of claim 37, wherein means for updating the biometric model for the individual comprises means for adjusting nominal and threshold values to represent information arising from responses to alert notifications.

48. The server of claim 37, further comprising means for determining an exception condition comprises means for determining an exception condition based upon determining that the current biometric sensor data describes biometric measurements that are outside a nominal range of a biometric parameter in a manner that suggests illness or injury.

49. The server of claim 37, wherein means for determining an exception condition comprises means for using characteristics of the exception condition.

50. The server of claim 37, wherein means for transmitting an alert notification in response to determining the exception condition comprises means for sending one of electronic, symbolic, or telephonic communications.

51. The server of claim 37, wherein means for transmitting an alert notification in response to determining the exception condition comprises means for sending communications to more than one recipient.

52. The server of claim 37, further comprising means for transmitting additional alert notifications in response to adjustments of alert levels based upon changes in the exception condition.

53. The server of claim 37, further comprising means for determining the alert notification for transmission by evaluating responses to previous alert notifications transmitted in response to previous exception conditions similar to the exception condition.

54. The server of claim 37, wherein the biometric sensor data evaluated and used in updating the biometric model comprises one or more of temperature, acceleration, pulse rate, blood pressure, blood oxygen level, blood sugar level, pH of skin, and presence of perspiration.

55. A non-transitory server-readable storage medium having stored thereon server processor-executable instructions configured to cause a server processor to perform operations for monitoring a population of individuals for health and safety, the operations comprising:
generating a biometric model of nominal and threshold biometric parameters for each individual of a population based on biometric sensor data obtained from a plurality of wireless biometric sensor devices which are attached to the individuals of the population and comprise one or more biometric sensors;
receiving current biometric sensor data from the plurality of wireless biometric sensor devices;
associating the current biometric sensor data received from each mobile device with a respective individual;
evaluating the current biometric sensor data for the individual using the biometric model for that individual;
determining an exception condition when the current biometric sensor data is outside of a nominal range of at least one biometric parameter for the individual;
transmitting an alert notification in response to determining the exception condition; and
updating the biometric model for the individual based on the current biometric sensor data,
wherein the generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of physical location of each individual.

56. The non-transitory server-readable storage medium of claim 55, wherein the stored server processor-executable software instructions are configured to cause a server processor to perform operations such that generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of temporal conditions.

57. The non-transitory server-readable storage medium of claim 56, wherein:
the stored server processor-executable software instructions are configured to cause a server processor to perform operations further comprising determining temporal conditions at the time the current biometric sensor data is transmitted to the server; and
the stored server processor-executable software instructions are configured to cause a server processor to perform operations such that evaluating the current biometric sensor data for the individual using the biometric model for that individual comprises comparing the current biometric sensor data for the individual to nominal ranges of the biometric parameters for that individual in temporal conditions similar to those of the temporal conditions at the time the current biometric sensor data is transmitted to the server.

58. The non-transitory server-readable storage medium of claim 55, wherein the stored server processor-executable software instructions are configured to cause a server processor to perform operations such that generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of scheduled activities.

59. The non-transitory server-readable storage medium of claim 58, wherein:
the stored server processor-executable software instructions are configured to cause a server processor to perform operations further comprising determining scheduled activities for the population of individuals at the time the current biometric sensor data is transmitted to the server; and
the stored server processor-executable software instructions are configured to cause a server processor to perform operations such that evaluating the current biometric sensor data for the individual using the biometric model for that individual comprises comparing the current biometric sensor data for the individual to nominal ranges of the biometric parameters during activities similar to the scheduled activities at the time the current biometric sensor data is transmitted to the server.

60. The non-transitory server-readable storage medium of claim 55, wherein the stored server processor-executable software instructions are configured to cause a server processor to perform operations such that generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of atmospheric conditions.

61. The non-transitory server-readable storage medium of claim 60, wherein:
the stored server processor-executable software instructions are configured to cause a server processor to perform operations further comprising determining the atmospheric conditions for the population of individuals at the time the current biometric sensor data is transmitted to the server; and
the stored server processor-executable software instructions are configured to cause a server processor to perform operations such that evaluating the current biometric sensor data for the individual using the biometric model for that individual comprises comparing the current biometric sensor data for the individual to nominal ranges of the biometric parameters for that individual in atmospheric conditions similar to those of the atmospheric conditions at the time the current biometric sensor data is transmitted to the server.

62. The non-transitory server-readable storage medium of claim 55, wherein:
the stored server processor-executable software instructions are configured to cause a server processor to perform operations further comprising determining the physical location of the individuals in the population at the time the current biometric sensor data is transmitted to the server; and
the stored server processor-executable software instructions are configured to cause a server processor to perform operations such that evaluating the current biometric sensor data for each respective individual using the biometric model for that individual comprises comparing the current biometric sensor data for each respective individual to nominal ranges of the biometric parameters for that individual while at the physical location at the time the current biometric sensor data is transmitted to the server.

63. The non-transitory server-readable storage medium of claim 55, wherein the stored server processor-executable software instructions are configured to cause a server processor to perform operations such that generating a biometric model of nominal and threshold biometric parameters for each individual of a population based on biometric sensor data obtained from a plurality of wireless biometric sensor devices comprises analyzing received biometric sensor data for each individual over a period of time to identify dependencies between various biometric parameters.

64. The non-transitory server-readable storage medium of claim 55, wherein the stored server processor-executable software instructions are configured to cause a server processor to perform operations such that updating the biometric model for the individual comprises adjusting nominal and threshold values to represent the current biometric sensor data.

65. The non-transitory server-readable storage medium of claim 55, wherein the stored server processor-executable software instructions are configured to cause a server processor to perform operations such that updating the biometric model for the individual comprises adjusting nominal and threshold values to represent information arising from responses to alert notifications.

66. The non-transitory server-readable storage medium of claim 55, wherein the stored server processor-executable software instructions are configured to cause a server processor to perform operations further comprising determining an exception condition based upon determining that the current biometric sensor data describes biometric measurements that are outside a nominal range of a biometric parameter in a manner that suggests illness or injury.

67. The non-transitory server-readable storage medium of claim 55, wherein the stored server processor-executable software instructions are configured to cause a server processor to perform operations further comprising determining the alert notification for transmission based on characteristics of the exception condition.

68. The non-transitory server-readable storage medium of claim 55, wherein the stored server processor-executable software instructions are configured to cause a server processor to perform operations such that transmitting an alert notification in response to determining the exception condition comprises sending one of electronic, symbolic, or telephonic communications.

69. The non-transitory server-readable storage medium of claim 55, wherein the stored server processor-executable software instructions are configured to cause a server processor to perform operations such that transmitting an alert notification in response to determining the exception condition comprises sending communications to more than one recipient.

70. The non-transitory server-readable storage medium of claim 55, wherein the stored server processor-executable software instructions are configured to cause a server processor to perform operations further comprising transmitting additional alert notifications in response to adjustments of alert levels based upon changes in the exception condition.

71. The non-transitory server-readable storage medium of claim 55, wherein the stored server processor-executable software instructions are configured to cause a server processor to perform operations further comprising determining the alert notification for transmission by evaluating responses to previous alert notifications transmitted in response to previous exception conditions similar to the exception condition.

72. The non-transitory server-readable storage medium of claim 55, wherein the stored server processor-executable software instructions are configured to cause a server processor to perform operations such that the biometric sensor data evaluated and used in updating the biometric model comprises one or more of temperature, acceleration, pulse rate, blood pressure, blood oxygen level, blood sugar level, pH of skin, and presence of perspiration.

73. A system, comprising:
a server comprising:
a memory; and
a server processor coupled to the memory and configured with server processor-executable instructions to perform operations comprising:
generating a biometric model of nominal and threshold biometric parameters for each individual of a population based on biometric sensor data obtained from a plurality of wireless biometric sensor devices which are attached to the individuals of the population and comprise one or more biometric sensors;
receiving current biometric sensor data from the plurality of wireless biometric sensor devices;
associating the current biometric sensor data received from each mobile device with a respective individual;
evaluating the current biometric sensor data for the individual using the biometric model for that individual;
determining an exception condition when the current biometric sensor data is outside of a nominal range of at least one biometric parameter for the individual;
transmitting an alert notification in response to determining the exception condition; and
updating the biometric model for the individual based on the current biometric sensor data,
wherein the generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of physical location of each individual.

74. The system of claim 73, wherein the server processor is configured with server processor-executable instructions to perform operations such that generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of temporal conditions.

75. The system of claim 74, wherein:
the server processor is configured with server processor-executable instructions to perform operations further comprising determining temporal conditions at the time the current biometric sensor data is transmitted to the server; and
the server processor is configured with server processor-executable instructions such that evaluating the current biometric sensor data for the individual using the biometric model for that individual comprises comparing the current biometric sensor data for the individual to nominal ranges of the biometric parameters for that individual in temporal conditions similar to those of the temporal conditions at the time the current biometric sensor data is transmitted to the server.

76. The system of claim 73, wherein the server processor is configured with server processor-executable instructions to perform operations such that generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of scheduled activities.

77. The system of claim 76, wherein:
the server processor is configured with server processor-executable instructions to perform operations further comprising determining scheduled activities for the population of individuals at the time the current biometric sensor data is transmitted to the server; and
the server processor is configured with server processor-executable instructions such that evaluating the current biometric sensor data for the individual using the biometric model for that individual comprises comparing the current biometric sensor data for the individual to nominal ranges of the biometric parameters during activities similar to the scheduled activities at the time the current biometric sensor data is transmitted to the server.

78. The system of claim 73, wherein the server processor is configured with server processor-executable instructions to perform operations such that generating a biometric model of nominal and threshold biometric parameters for each individual of a population based on biometric sensor data obtained from a plurality of wireless biometric sensor devices comprises analyzing received biometric sensor data for each individual over a period of time to calculate average and threshold values for each biometric parameter as a function of atmospheric conditions.

79. The system of claim 78, wherein:
the server processor is configured with server processor-executable instructions to perform operations further comprising determining the atmospheric conditions for the population of individuals at the time the current biometric sensor data is transmitted to the server; and
the server processor is configured with server processor-executable instructions such that evaluating the current biometric sensor data for the individual using the biometric model for that individual comprises comparing the current biometric sensor data for the individual to nominal ranges of the biometric parameters for that individual in atmospheric conditions similar to those of the atmospheric conditions at the time the current biometric sensor data is transmitted to the server.

80. The system of claim 73, wherein:
the server processor is configured with server processor-executable instructions to perform operations further comprising determining the physical location of the individuals in the population at the time the current biometric sensor data is transmitted to the server; and
the server processor is configured with server processor-executable instructions such that evaluating the current biometric sensor data for each respective individual using the biometric model for that individual comprises comparing the current biometric sensor data for each respective individual to nominal ranges of the biometric parameters for that individual while at the physical location at the time the current biometric sensor data is transmitted to the server.

81. The system of claim 73, wherein the server processor is configured with server processor-executable instructions to perform operations such that generating a biometric model of nominal and threshold biometric parameters for each individual of a population based on biometric sensor data obtained from a plurality of wireless biometric sensor devices comprises analyzing received biometric sensor data for each individual over a period of time to identify dependencies between various biometric parameters.

82. The system of claim 73, wherein the server processor is configured with server processor-executable instructions such that updating the biometric model for the individual comprises adjusting nominal and threshold values to represent the current biometric sensor data.

83. The system of claim 73, wherein the server processor is configured with server processor-executable instructions such that updating the biometric model for the individual comprises adjusting nominal and threshold values to represent information arising from responses to alert notifications.

84. The system of claim 73, wherein the server processor is configured with server processor-executable instructions to perform operations further comprising determining an exception condition based upon determining that the current biometric sensor data describes biometric measurements that are outside a nominal range of a biometric parameter in a manner that suggests illness or injury.

85. The system of claim 73, wherein the server processor is configured with server processor-executable instructions to perform operations further comprising determining the alert notification for transmission based on characteristics of the exception condition.

86. The system of claim 73, wherein the server processor is configured with server processor-executable instructions such that transmitting an alert notification in response to determining the exception condition comprises sending one of electronic, symbolic, or telephonic communications.

87. The system of claim 73, wherein the server processor is configured with server processor-executable instructions such that transmitting an alert notification in response to determining the exception condition comprises sending communications to more than one recipient.

88. The system of claim 73, wherein the server processor is configured with server processor-executable instructions to perform operations further comprising transmitting additional alert notifications in response to adjustments of alert levels based upon changes in the exception condition.

89. The system of claim 73, wherein the server processor is configured with server processor-executable instructions to perform operations further comprising determining the alert notification for transmission by evaluating responses to previous alert notifications transmitted in response to previous exception conditions similar to the exception condition.

90. The system of claim 73, wherein the server processor is configured with server processor-executable instructions to perform operations such that the biometric sensor data evaluated and used in updating the biometric model comprises one or more of temperature, acceleration, pulse rate, blood pressure, blood oxygen level, blood sugar level, pH of skin, and presence of perspiration.

* * * * *